United States Patent
Syed Khuzzan et al.

(10) Patent No.: US 11,092,935 B2
(45) Date of Patent: Aug. 17, 2021

(54) SIMPLIFIED LOGIC INJECTION CONTROL (SLIC) FOR DEMULSIFIER CHEMICAL AUTOMATION

(71) Applicant: Saudi Arabian Oil Company, Dhahran (SA)

(72) Inventors: Syed Haizir Syed Khuzzan, Udhailiyah (SA); Marnix Jan Teuling, Udhailiyah (SA); Randall L. Franklin, Udhailiyah (SA)

(73) Assignee: Saudi Arabian Oil Company, Dhahran (SA)

( * ) Notice: Subject to any disclaimer, the term of this patent is extended or adjusted under 35 U.S.C. 154(b) by 435 days.

(21) Appl. No.: 16/052,163

(22) Filed: Aug. 1, 2018

(65) Prior Publication Data
US 2020/0040263 A1  Feb. 6, 2020

(51) Int. Cl.
*G05B 13/04* (2006.01)
*C10G 33/04* (2006.01)
(Continued)

(52) U.S. Cl.
CPC ........ *G05B 13/041* (2013.01); *B01D 11/0484* (2013.01); *B01D 17/02* (2013.01);
(Continued)

(58) Field of Classification Search
CPC .. B01D 17/12; B01D 17/047; B01D 17/0208; B01D 21/34; B01D 11/0446;
(Continued)

(56) References Cited

U.S. PATENT DOCUMENTS 581,134 A  4/1897 Poole
4,581,134 A  4/1986 Richter et al.
(Continued)

OTHER PUBLICATIONS

A. Alshehri (Modeling and Optimization of Desalting Process in Oil Industry, University of Waterloo thesis) (Year: 2009).*
(Continued)

*Primary Examiner* — Dean Kwak
(74) *Attorney, Agent, or Firm* — Fish & Richardson P.C.

(57) ABSTRACT

Systems and techniques for demulsifier automation of the wet crude handling facilities can include a computer-implemented method. Demulsifier automation parameters for automating demulsifier injection points of a wet crude handling facility are determined. The determining includes performing a data convolution and a smoothening of inlet demulsifier automation parameters. Performing the demulsifier automation of the wet crude handling facility, includes, for each demulsifier, the following: A current state of the demulsifier is identified based on the demulsifier automation parameters. Demulsifier calculation input parameters are determined, including performing a convolution and a smoothening of the demulsifier calculation input parameters. A demulsifier dosage rate is calculated using the determined demulsifier calculation input parameters. A state dependent dosage multiplication factor is applied to the demulsifier based on the current state based on the calculated demulsifier dosage rate.

8 Claims, 20 Drawing Sheets

(51) Int. Cl.
- *B01D 17/02* (2006.01)
- *G01N 33/28* (2006.01)
- *C10G 33/00* (2006.01)
- *B01D 11/04* (2006.01)
- *C10G 33/08* (2006.01)
- *B01D 21/34* (2006.01)
- *C10G 31/08* (2006.01)
- *G01N 13/00* (2006.01)
- *B01D 17/12* (2006.01)

(52) U.S. Cl.
CPC ......... *B01D 17/0208* (2013.01); *B01D 21/34* (2013.01); *C10G 33/00* (2013.01); *C10G 33/04* (2013.01); *C10G 33/08* (2013.01); *G01N 33/2823* (2013.01); *B01D 11/0446* (2013.01); *B01D 17/12* (2013.01); *C10G 31/08* (2013.01); *C10G 2300/205* (2013.01); *G01N 13/00* (2013.01)

(58) Field of Classification Search
CPC .... B01D 11/0484; B01D 17/02; C10G 33/08; C10G 31/08; C10G 33/04; C10G 33/00; C10G 2300/205; G01N 33/2823; G01N 13/00; G05B 13/041
See application file for complete search history.

(56) References Cited

U.S. PATENT DOCUMENTS

| | | | |
|---|---|---|---|
| 9,255,228 B2* | 2/2016 | Prasad | B01D 17/04 |
| 9,555,345 B2 | 1/2017 | Al-Shafei et al. | |
| 2014/0131254 A1 | 5/2014 | Soliman | |
| 2016/0186562 A1* | 6/2016 | Lee | G06Q 50/02 |
| | | | 702/6 |
| 2018/0195010 A1* | 7/2018 | Salu | C10G 31/08 |
| 2019/0062645 A1* | 2/2019 | Al Seraihi | B01D 17/047 |

OTHER PUBLICATIONS

Al-Amri et at., "Lean Six Sigma study for demulsifier optimization and minimizing dehydrators low voltages at SGPD facilities," SGED/HHPEU-018, Jan. 17, 2009, 68 pages.

Saudi Arabian Oil Company (Saudi Aramco), "Sample SGPD GOSP OIM (Demulsifier Automation section)," Dec. 29, 2008, 11 pages.

International Search Report and Written Opinion issued in International Application No. PCT/US2019/044027 dated Nov. 13, 2019, 17 pages.

GCC Examination Report in GCC Appln. No. GC 2019-38021, dated Oct. 21, 2020, 5 pages.

GCC Examination Report in GCC Appln. No. GC 2019-3 8021, dated May 27, 2021, 3 pages.

* cited by examiner

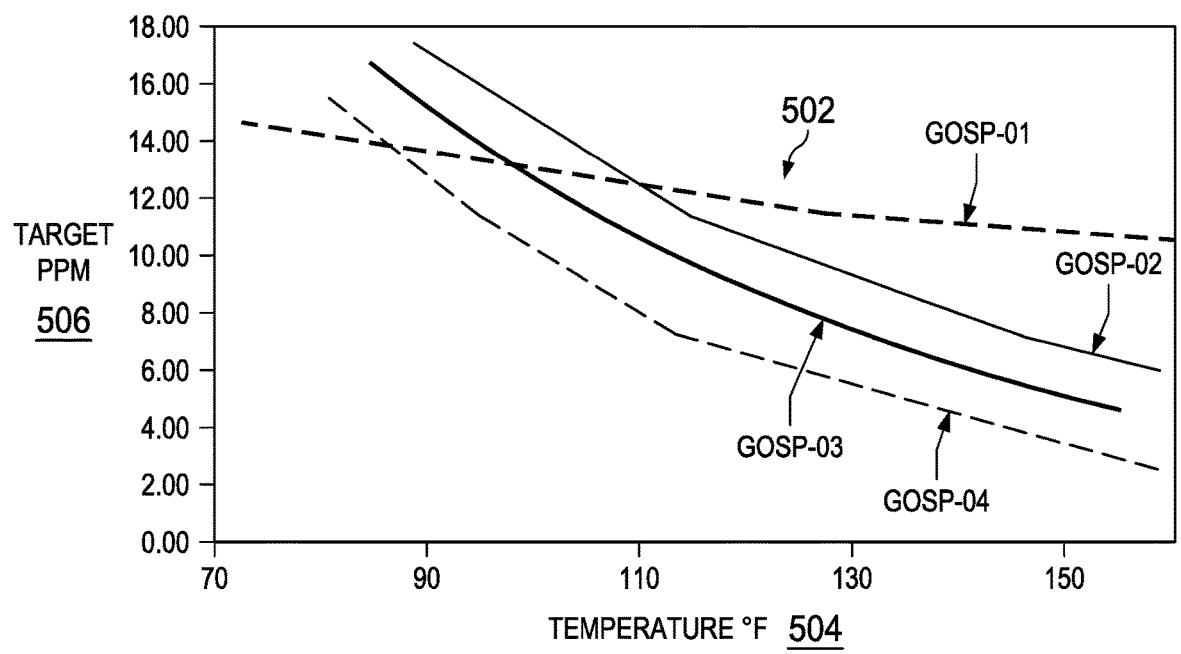
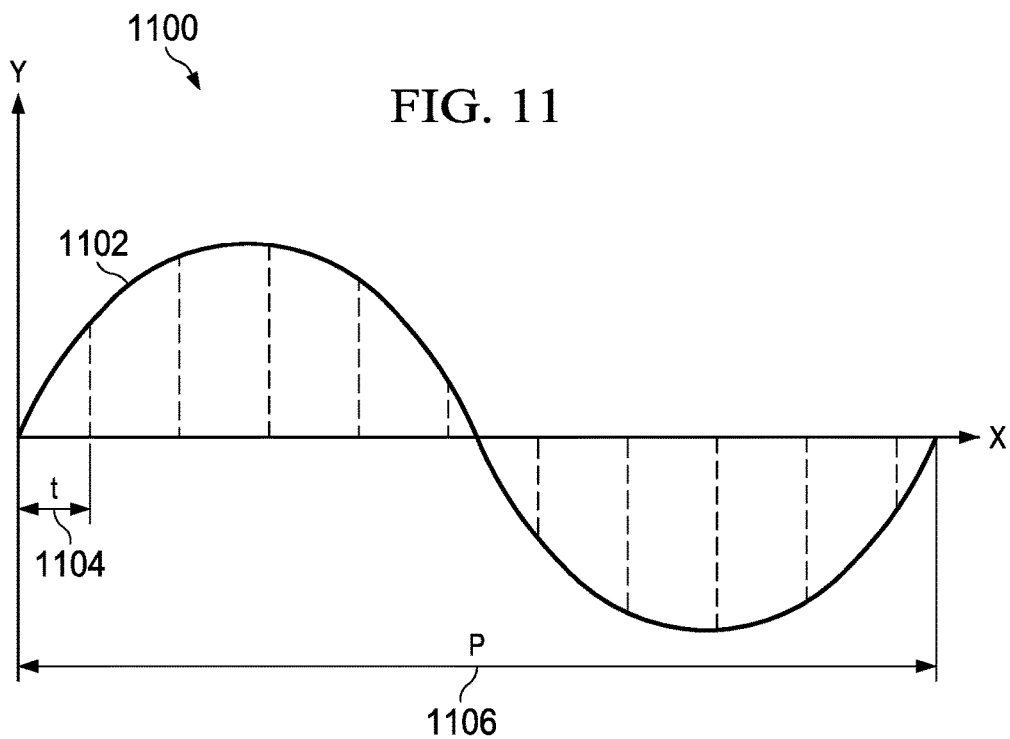

FROM FIG. 13A

DEMULSIFIER CONTROL SETTINGS

| DESCRIPTION | | UOM | CCCCCCCCC DEH. INLET | CCCCCCCCC PROD. HDR1 | CCCCCCCCC PROD. HDR2 |
|---|---|---|---|---|---|
| PROCESS CONDITION | | N/A | XXXXXXX | XXXXXXX | XXXXXXX |
| NORMAL STATE MULTIPLIER | | N/A | RR.RR | RR.RR | RR.RR |
| ABNORMAL STATE MULTIPLIER | | N/A | RR.RR | RR.RR | RR.RR |
| TARGET SETPOINT | | CCCCCC | RRRR.R | RRRR.R | RRRR.R |
| CURRENT SETPOINT | | CCCCCC | RRRR.R | RRRR.R | RRRR.R |
| DIFFERENCE (TARGET - CURRENT) | | CCCCCC | RRRR.R | RRRR.R | RRRR.R |
| VALUE TO TRANSITION TO NORMAL | | CCCCCC | RRR.R | RRRR.R | RRRR.R |
| DEMULSIFIER INJECTION FLOW CONTROLLER | MODE | N/A | ☞ CCC | ☞ CCC | ☞ CCC |
| | PV | CCCCCC | RRRR.R | RRRR.R | RRRR.R |
| | SV | CCCCCC | RRRR.R | RRRR.R | RRRR.R |
| | MV | CCCCCC | RRRR.R | RRRR.R | RRRR.R |

| TOTAL DEMULSIFIER FLOW |
|---|
| RRRR.R CCC |

PROCESS PARAMETERS

| DESCRIPTION | UOM | RAW PV | AVG |
|---|---|---|---|
| CRUDE TEMPERATURE | CCCCCC | RRRR.R | RRRR.R |
| NET LIQUID FLOW | CCCCCC | RRRR.R | RRRR.R |
| DEHYDRATION GRID VOLTAGE | CCCCCC | RRRRRR | RRRRRR |
| DESALTER GRID VOLTAGE | CCCCCC | RRRRRR | RRRRRR |
| BS&W READING | CCCCCC | R.RRR | R.RRR |

NET LIQUID FLOW CONVOLUTION (CURVE SMOOTHING)

| DESCRIPTION | PARAMETER | VALUE | UOM |
|---|---|---|---|
| RESET TIMER | PV | RRRRR | SEC |
|  | PH | RRRRR | SEC |
| CUMULATIVE AVG (INITIAL STEP) | CPV | RRRR.R | MBD |
|  | PREV | RRRR.R | MBD |
| ROLLING AVERAGE (SECOND STEP) | CPV | RRRR.R | MBD |
|  | SMPL | RRR | SEC |
|  | NUM | RR |  |

CRUDE TEMPERATURE CONVOLUTION (CURVE SMOOTHING)

| DESCRIPTION | PARAMETER | VALUE | UOM |
|---|---|---|---|
| RESET TIMER | PV | RRRRR | SEC |
|  | PH | RRRRR | SEC |
| CUMULATIVE AVG (INITIAL STEP) | CPV | RRRR.R | MBD |
|  | PREV | RRRR.R | MBD |
| ROLLING AVERAGE (SECOND STEP) | CPV | RRRR.R | MBD |
|  | SMPL | RRR | SEC |
|  | NUM | RR |  |

DEMULSIFIER ENGINEERING PARAMETERS ENTRY

FLOW CONTROLLER PARAMETERS

| PARAM | UOM | CCCCCCC DCH INLET | CCCCCCC PROD HDR1 | CCCCCCC PROD HDR2 |
|---|---|---|---|---|
| CONDITION | N/A | XXXXXXX | XXXXXXX | XXXXXXX |
| MODE | N/A | CCC | CCC | CCC |
| PV | CCCCCC | RRRR.R | RRRR.R | RRRR.R |
| SV | CCCCCC | RRRR.R | RRRR.R | RRRR.R |
| MV | CCCCCC | RRRR.R | RRRR.R | RRRR.R |

| DEMULSIFIER CONTROL SETTINGS | | | | | | |
|---|---|---|---|---|---|---|
| | DESCRIPTION | UOM | CCCCCCC DEH INLET | CCCCCCC PROD HDR1 | CCCCCCC PROD HDR2 | |
| NORMAL CONDITION | MULTIPLY FACTOR | N/A | 👇 RR.RR | 👇 RR.RR | 👇 RR.RR | |
| | VELOCITY LIMIT UP (DMVP) | CCCCCCC | 👇 R.RRR | 👇 R.RRR | 👇 R.RRR | |
| | VELOCITY LIMIT DOWN (DMVM) | CCCCCCC | 👇 R.RRR | 👇 R.RRR | 👇 R.RRR | |
| TRANSIT CONDITION | MULTIPLY FACTOR | N/A | 👇 RR.RR | 👇 RR.RR | 👇 RR.RR | |
| | VELOCITY LIMIT UP (DMVP) | CCCCCCC | 👇 R.RRR | 👇 R.RRR | 👇 R.RRR | |
| | VELOCITY LIMIT DOWN (DMVM) | CCCCCCC | 👇 R.RRR | 👇 R.RRR | 👇 R.RRR | |
| ABNORMAL CONDITION | MULTIPLY FACTOR | N/A | 👇 RR.RR | 👇 RR.RR | 👇 RR.RR | |
| | VELOCITY LIMIT UP (DMVP) | CCCCCCC | 👇 R.RRR | 👇 R.RRR | 👇 R.RRR | |
| | VELOCITY LIMIT DOWN (DMVM) | CCCCCCC | 👇 R.RRR | 👇 R.RRR | 👇 R.RRR | |
| VELOCITY LIMITER | SV (CALCULATED) | CCCCCC | RRRR.R | RRRR.R | RRRR.R | |
| | SV (INPUT TO VELLIM) | CCCCCC | RRRR.R | RRRR.R | RRRR.R | |
| | MV (OUTPUT FROM VELLIM) | CCCCCC | RRRR.R | RRRR.R | RRRR.R | |
| | DV (DIFFERENCE IN SV & MV) | CCCCCC | R.RRR | R.RRR | R.RRR | |
| | CURRENT VELOCITY LIMIT UP (DMVP) | CCCCCCC | R.RRR | R.RRR | R.RRR | |
| | CURRENT VELOCITY LIMIT UP (DMVM) | CCCCCCC | R.RRR | R.RRR | R.RRR | |
| TRANSIT SETPOINT | % TO SWITCH TRANSIT TO NORMAL | % | 👇 RR.R | 👇 RR.R | 👇 RR.R | |
| | VALUE TO SWITCH TRANSIT TO NORMAL | CCCCCC | RRR.R | RRRR.R | RRRR.R | |

FROM FIG. 14A

| PROCESS SETPOINTS FOR ABNORMAL CONDITION | | | | |
|---|---|---|---|---|
| DESCRIPTION | UOM | TRIP | RESET | |
| DEHYDRATOR GRID SETPOINTS | CCCCCC | 👇 RRRRRR | 👇 RRRRRR | |
| DESALTER GRID SETPOINTS | CCCCCC | 👇 RRRRRR | 👇 RRRRRR | |
| BS&W ANALYZER SETPOINTS | CCCCCC | R.RRR | R.RRR | |

| PERFORMANCE INDICATORS | | | |
|---|---|---|---|
| DESCRIPTION | UOM | TARGET | ACTUAL |
| TOTAL DEMULS FLOW (NO FACTOR) | CCCCCC | RRRR.R | N/A |
| SAFETY MARGIN | N/A | RR.RR | RR.RR |
| TOTAL DEMULS FLOW (WITH FACTOR) | CCCCCC | RRRR.R | 👇 RRR.R |

SIMPLIFIED LOGIC INJECTION CONTROL (SLIC) FOR DEMULSIFIER CHEMICAL AUTOMATION

BACKGROUND

The oil industry uses demulsifiers that include various chemicals as emulsion breakers to separate emulsions (such as water in oil). For example, demulsifiers can be used in the processing of crude oil. Crude oil can contain, for example, quantities of salt water that need to be removed before refining in order to improve the refinement process and reduce potential corrosion problems. Demulsifiers can also be used to separate oil and water in an emulsion.

SUMMARY

The present disclosure describes techniques that can be used for demulsifier automation algorithm implementations in gas-oil separator plants (GOSPs).

In some implementations, a computer-implemented method includes: determining demulsifier automation parameters for automating demulsifier injection points of a wet crude handling facility, the determining including performing a data convolution and a smoothening of inlet demulsifier automation parameters; and performing the demulsifier automation of the wet crude handling facility, including, for each demulsifier: identifying a current state of the demulsifier, the identifying based on the demulsifier automation parameters; determining demulsifier calculation input parameters, including performing a convolution and a smoothening of the demulsifier calculation input parameters; calculating, using the determined demulsifier calculation input parameters, a demulsifier dosage rate; applying, to the demulsifier and based on the current state, a state dependent dosage multiplication factor based on the calculated demulsifier dosage rate.

The previously described implementation is implementable using a computer-implemented method; a non-transitory, computer-readable medium storing computer-readable instructions to perform the computer-implemented method; and a computer-implemented system comprising a computer memory interoperably coupled with a hardware processor configured to perform the computer-implemented method/the instructions stored on the non-transitory, computer-readable medium.

The subject matter described in this specification can be implemented in particular implementations, so as to realize one or more of the following advantages. First, improved demulsifier injection automation techniques can allow facilities to be more reliable and cost effective. Second, in addition to the automation techniques being simpler and more practical, the input parameters, including temperature and liquid flowrates, can be reduced and well-established. Third, the up-time of controller operations can be improved while still being fully compliant to the desired product specifications. Fourth, an improvement in operations can occur without degradation of the dehydrator and desalter grid operations. Fifth, results can be measured, tabulated, diagnosed, and analyzed for comparison with information from other time periods to capture seasonal variations, causes of upsets, and increased demulsifier usage. Sixth, the improved demulsifier injection automation scheme can make full use of existing equipment at a site. Seventh, product quality can remain stable even after boundary conditions are breached. Other advantages will be apparent to those of ordinary skill in the art.

The details of one or more implementations of the subject matter of this specification are set forth in the Detailed Description, the claims, and the accompanying drawings. Other features, aspects, and advantages of the subject matter will become apparent from the Detailed Description, the claims, and the accompanying drawings.

DESCRIPTION OF DRAWINGS

FIG. 5 is a graph showing examples of relationships between a temperature and a target parts per million (PPM), according to some implementations of the present disclosure.

FIG. 11 is a graph of an example of a sine wave, according to some implementations of the present disclosure.

FIGS. 13A-13B collectively show a screen print of an example of an operator interface for demulsifier injection automation, according to some implementations of the present disclosure.

FIGS. 14A-14B collectively show a screen print of an example of an engineering parameter entry interface 1400, according to some implementations of the present disclosure.

Like reference numbers and designations in the various drawings indicate like elements.

DETAILED DESCRIPTION

Figure 1A:
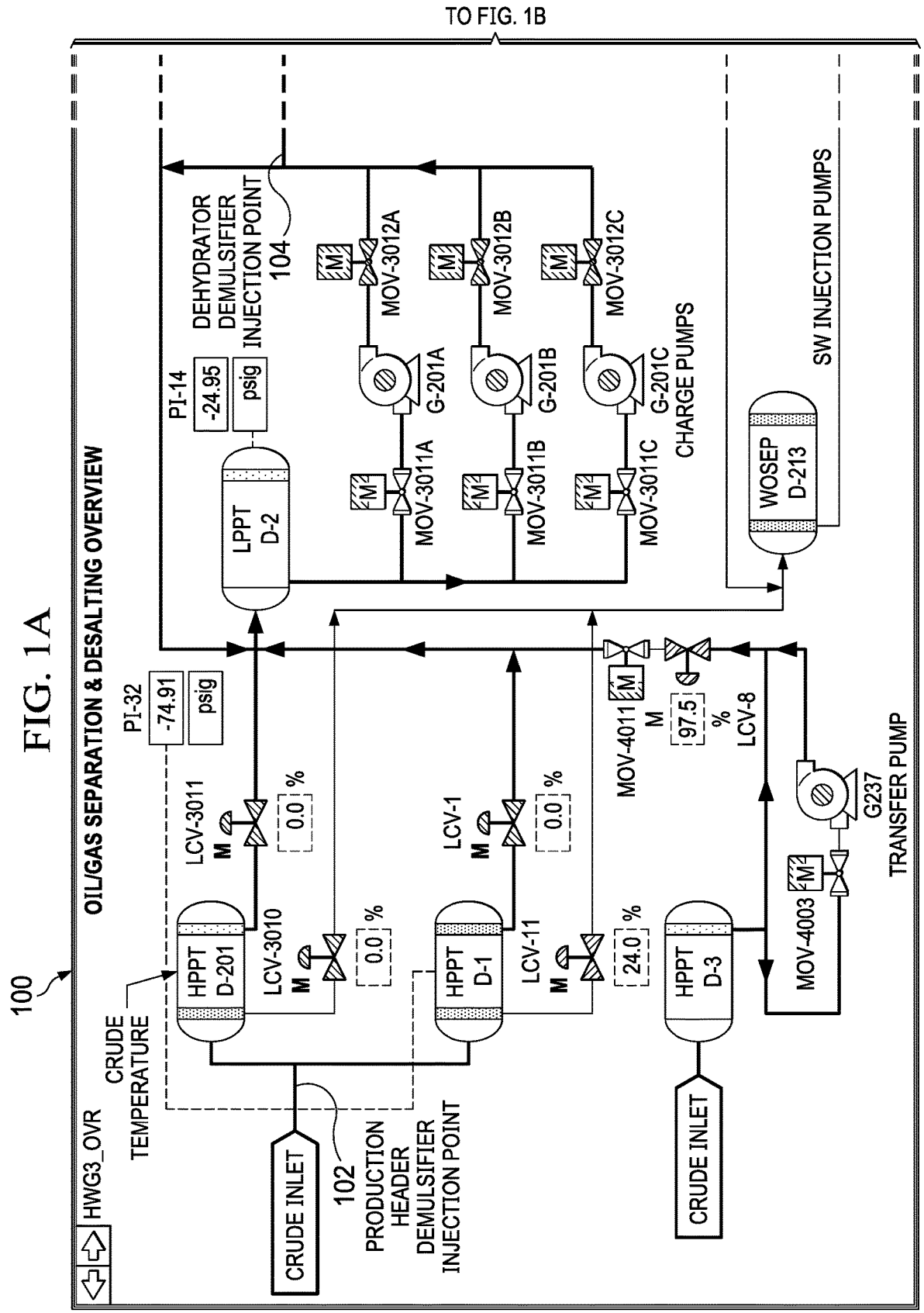
FIGS. 1A-1B are schematic diagrams collectively showing an example of a wet crude handling facility of a typical gas-oil separator plant (GOSP), according to some implementations of the present disclosure.

The following detailed description describes techniques for demulsifier automation algorithm implementations in gas-oil separator plants (GOSPs). Various modifications, alterations, and permutations of the disclosed implementations can be made and will be readily apparent to those or ordinary skill in the art, and the general principles defined may be applied to other implementations and applications, without departing from scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

Some conventional demulsifier automation algorithm implementations in GOSPs can be based on band severity with numerous parameter inputs, such as temperature, dehydrator voltage, desalter voltage, dehydrator water outlet flow, and basic sediment and water (BS&W) at the desalter outlet. Not only are the conventional implementations complicated, an initial starting point of calculations can involve a lot of guess work. For example, conventional implementations can be affected by rates of change in the different bands that may need to be seasonally adjusted for summer and winter, adjusted between day and night, and that are impacted by day-to-day GOSP operations. As a result, the conventional implementations may not work properly or may be sub-optimized, and the control loop may need to be operated in manual or semi-automatic mode most or all of the time. This can result in a tendency to overdose the demulsifier chemicals, which can subsequently result in a counterproductive re-emulsification of the process fluid. Simple conventional techniques for demulsifier injection are automatic with setpoint adjusted manually. More advanced techniques can be band-based, which can be unstable.

Field trials can be carried out to determine required demulsifier dosing rates depending on a variety of process parameters. As a result, curve fit equations of demulsifier performance are determined during the field trials. Resulting performance curves can indicate required dosages as a parts-per-million (PPM) function of temperature per million parts of crude and produced water or other parameters. The PPM function can then be combined with (for example, multiplied by) the GOSP total liquid rates to determine a required demulsifier injection rate with a unit conversion factor. Since the algorithm can be much simpler (for example, using a reduced set of input parameters) and can use well-established input parameters (for example, temperature and GOSP liquid flowrates), the algorithm can help to improve the up-time of demulsifier operations, including over harsh winter months. In addition to updating the algorithm logic for the continuous remote setpoint demulsifier automation, other changes can be made over time to assure that crude quality is always met and that intervention is achievable when a breach occurs in the boundary conditions. An environmental site assessment can be initiated to enhance and improve the existing demulsifier automation scheme to achieve the following benefits and control objectives: 1) effective and reliable automation scheme application; and 2) a simplified and easy-to-use automation application, including eliminating or minimizing operator intervention.

Figure 1B:
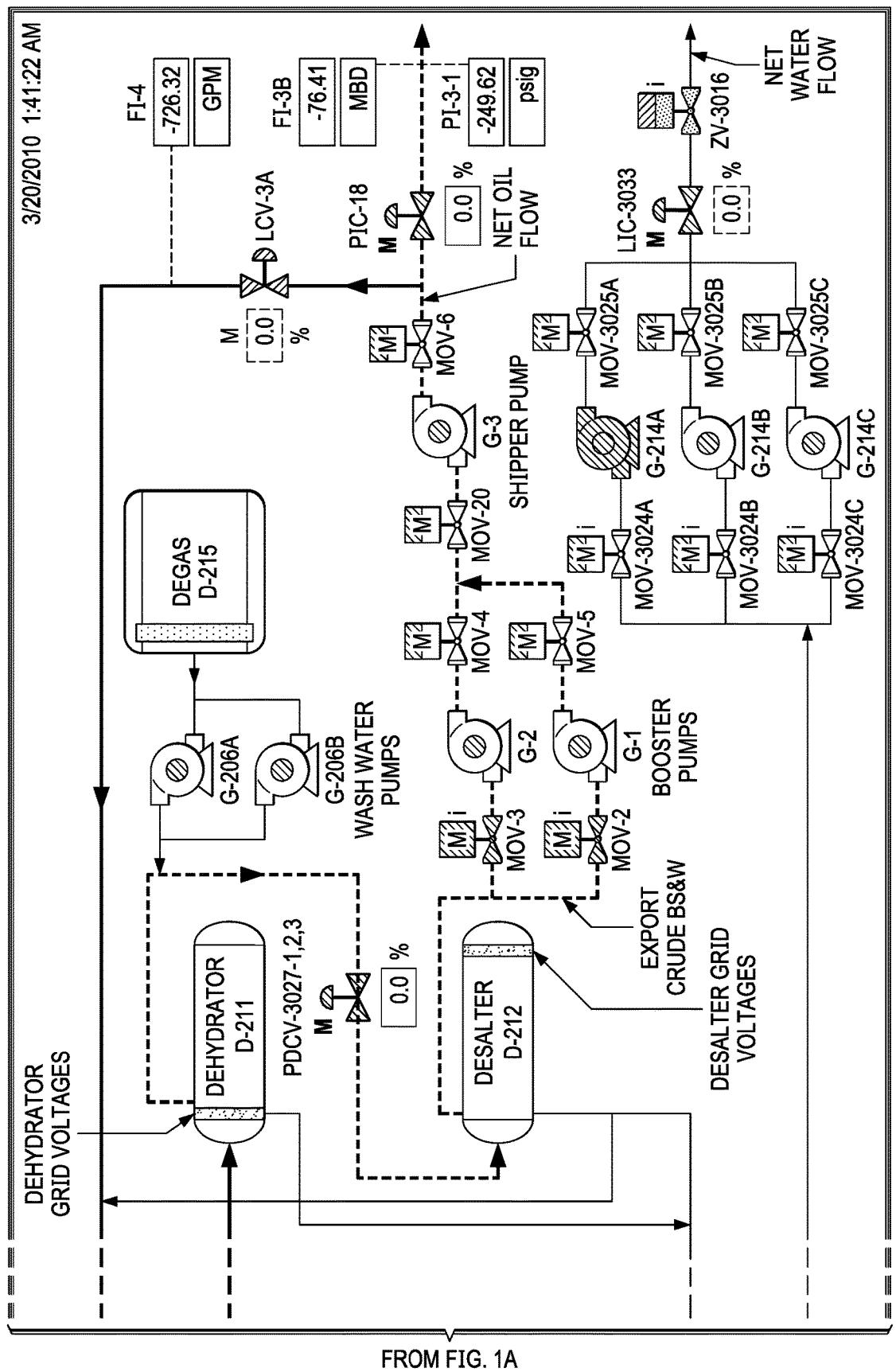

FIGS. 1A-1B are schematic diagrams collectively showing an example of a wet crude handling facility 100 of a typical GOSP, according to some implementations of the present disclosure. The diagram highlights main demulsifier injection points as well as input parameters that are used in the demulsifier automation.

A majority of the free water from the wells can be removed using the GOSPs gravity separators (for example, high-pressure separators (HPPT)). The dehydrator and desalter can separate water using electrostatic coalescence. A high electric potential can be applied across the internals. The water droplets suspended in the oil layer can be polarized by the applied electrical potential. As a result, the water droplet can become elongated, reducing the distance between the water droplets. The reduced distance can help in the flocculation and aggregation of droplets, facilitating the separation of water from the crude. Proper demulsifier dosing will assist in this process and improved performance of electrostatic coalescence. Demulsifier injection points can include an inlet header injection point 102 and a dehydrator inlet injection point 104.

The injected demulsifier can be used to break a boundary layer around water droplets so that small water droplets can coalesce together into larger sizes, thus making it easier to separate the water from the oil by gravitational forces. The ease of emulsion separation can be proportional to an original water droplet size and inversely proportional to a strength of the boundary layer around water droplets (for example, indicating emulsion tightness).

Figure 2:
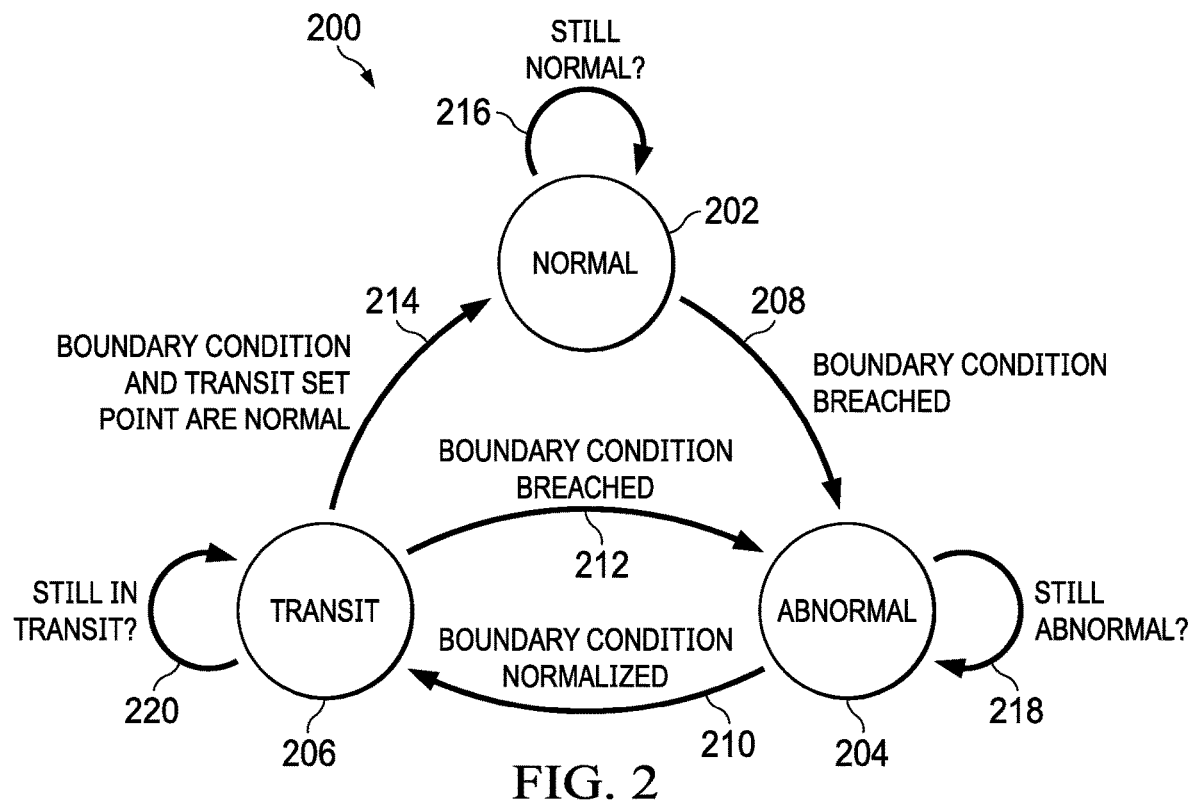
FIG. 2 is a diagram of an example of a demulsifier injection automation state diagram, according to some implementations of the present disclosure.

FIG. 2 is a diagram of an example of a demulsifier injection automation state diagram 200, according to some implementations of the present disclosure. The state diagram 200 includes a normal state 202, an abnormal state 204, and a transit state 206.

A methodology for demulsifier injection automation can as follows. First, data convolution and smoothening of inlet parameters is performed. The parameters can include, for example, dehydrator voltages, dehydrator voltages, and BS&W. Second, the result of the data convolution and smoothening of boundary parameters can be used as input for identifying a state (for example, one of the normal state 202, the abnormal state 204, or the transit state 206). Third, data convolution and smoothening of demulsifier calculation input parameters can be performed. The demulsifier calculation input parameters can include, for example, crude temperature and GOSP total liquid flowrates, which are a sum of net crude export and net water injection rates. Fourth, demulsifier dosage rate calculation can be performed. Fifth, a dosage multiplication factor (for example, that is state dependent) can be applied. The selected margin can help to smoothen out sporadic process upset surges that may otherwise be uncontrolled. In some implementations, as shown in the state diagram, when the current state is the abnormal state 204, returning to the normal state 202 cannot occur without first going through the transit state 206. This can provide for a controlled reduction and ramping down of the demulsifier flowrate, including slowly weaning the process of the excess demulsifier, so as to minimize the relapse from the transit to abnormal state 204, and vice versa.

Figure 3:
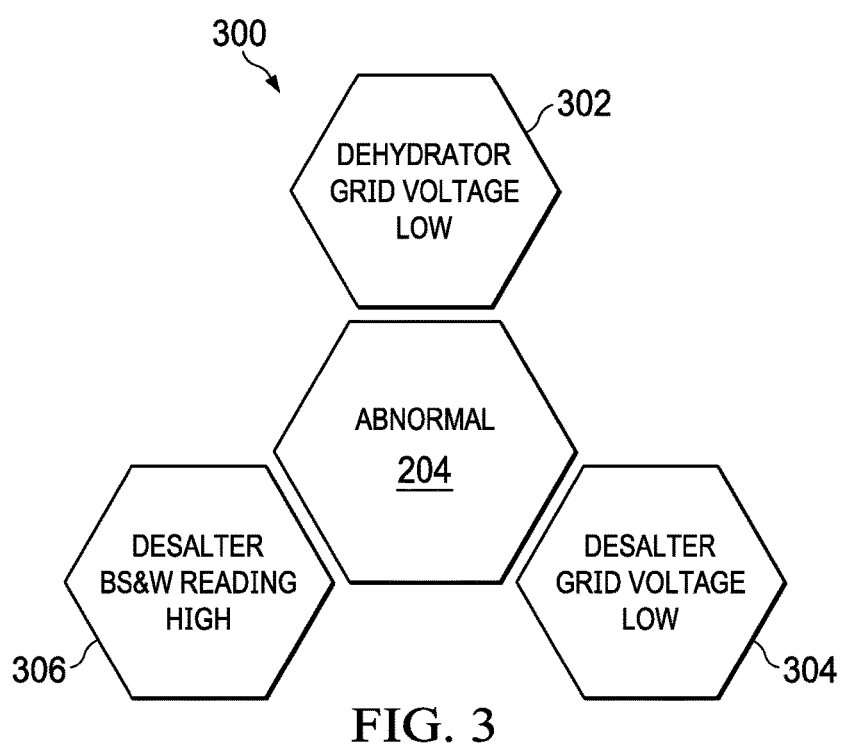
FIG. 3 is a block diagram showing examples of conditions leading to the abnormal state, according to some implementations of the present disclosure.

FIG. 3 is a block diagram showing examples of conditions leading to the abnormal state 204, according to some implementations of the present disclosure. For example, a boundary condition breach 208 that results in a transition to an abnormal state 204 can be any one of the following conditions: a dehydrator grid voltage low condition 302, a desalter grid voltage low condition 304, and a desalter BS&W reading high condition 306.

Referring again to FIG. 2, a boundary condition normalized event 210 can cause a state transition from the abnormal state 204 to the transit state 206. A boundary condition breach event 212 can cause a state transition from the transit state 206 to the abnormal state 204. A determination 214 that the boundary condition and transit setpoint are normal can cause a state transition from the transit state 206 to the normal state 202. A still normal determination 216 can cause the normal state 202 to stay in effect. A still abnormal determination 218 can cause the abnormal state 204 to stay in effect. A still in transit determination 220 can cause the transit state 206 to stay in effect.

Trouble and normalization settings for the boundary conditions are stored as constant values. Whenever the boundary conditions are breached 208, a state transition can occur to the abnormal state 204, and the dosage multiplication factors given in Table 1 can be applied. The dosage multiplication factors can be configurable.

TABLE 1

Dosage Multiplication Factors

| State | Production Header Multiplier | Dehydrator Inlet Multiplier |
|---|---|---|
| Normal | N1 | N2 |
| Abnormal | A1 | A2 |
| Transit | T1 | T2 |

In some implementations, when the current state is the transit state, injection rates can be reduced, for example, by 60 gallons per hour (GPH) until a transient setpoint is reached. All three states (normal, abnormal, and transit) can require the demulsifier dosage rate to be calculated. In some implementations, the input parameters required for the dosage rate calculation can include a crude temperature and GOSP total liquid flow rates.

Figure 4:
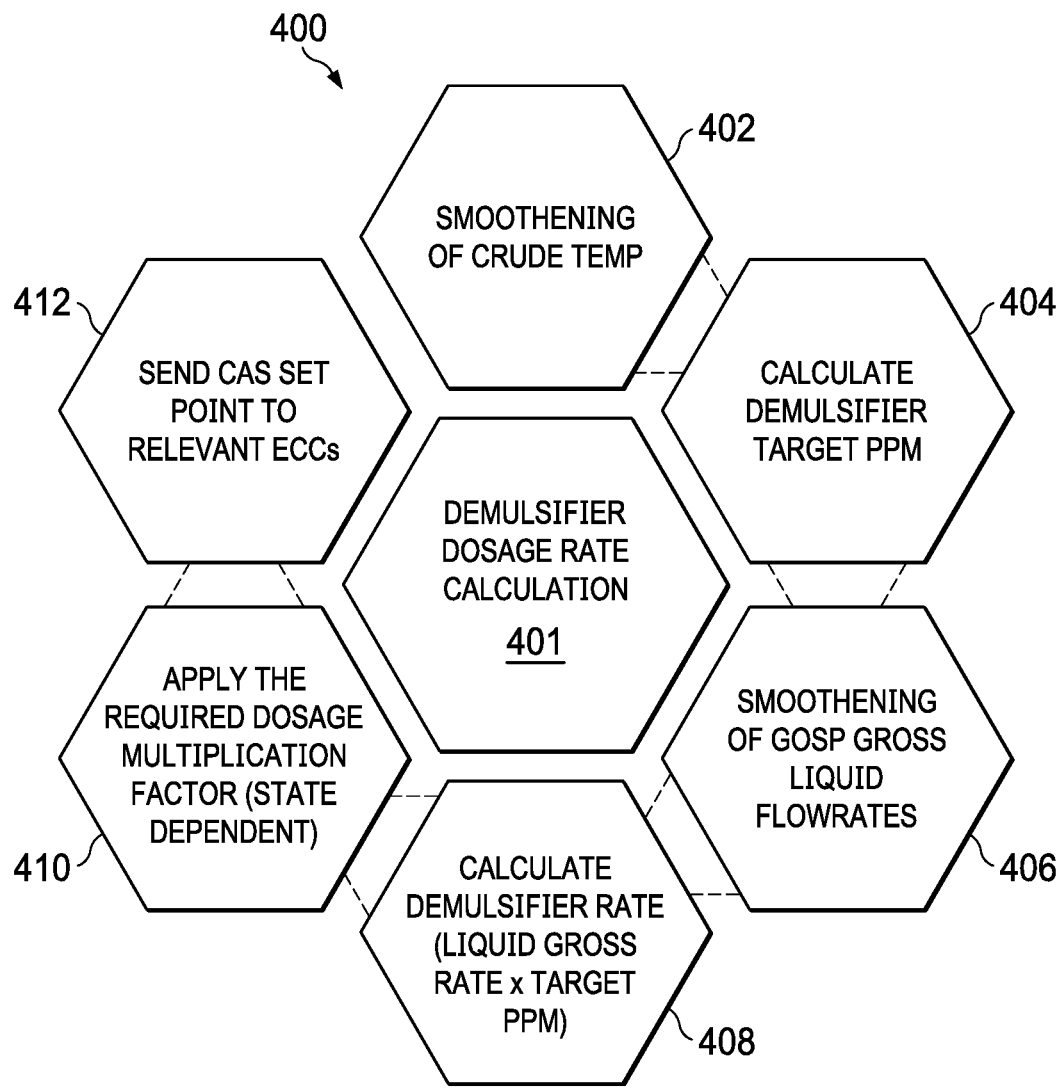
FIG. 4 is a flow diagram of an example of a process for calculating the demulsifier dosage rate, according to some implementations of the present disclosure.

FIG. 4 is a flow diagram of an example of a process 400 for calculating the demulsifier dosage rate 401, according to some implementations of the present disclosure. The process 400 can be based, for example, on methodologies used to validate demulsifier key performance indicators (KPIs).

At 402, a smoothened value of a crude temperature, x (for example, 110 deg. F.), is looked up. At 404, a target PPM y (for example, target PPM=11) is calculated. At 406, smoothening of GOSP liquid flowrates is performed. At 408, a demulsifier rate (gallons per day (GPD)) is calculated, for example, as a product of the liquid gross rate and the calculated target PPM, times a conversion factor. At 410, a dosage multiplication factor is applied (for example, that is state dependent). At 412, the CAS setpoint is set to a product of the calculated demulsifier rate (GPD) and the state multiplier.

In some implementations, typical field instrumentation set up in GOSPs for demulsifier automation can include: 1) one or more positive displacement pumps (for example, dual head) with electronic capacity controllers (ECCs), and 2) a Coriolis Mass flowmeter.

FIG. 5 is a graph 500 showing example relationships 502 between a temperature 504 and a target PPM 506, according to some implementations of the present disclosure. For example, the graph 500 can be based on field trial results. The relationships 502 correspond to samples for specific GOSPs to show relationships between demulsifier target PPM vs temperature. Different GOSPs may have different curves for the same temperature.

Figure 6:
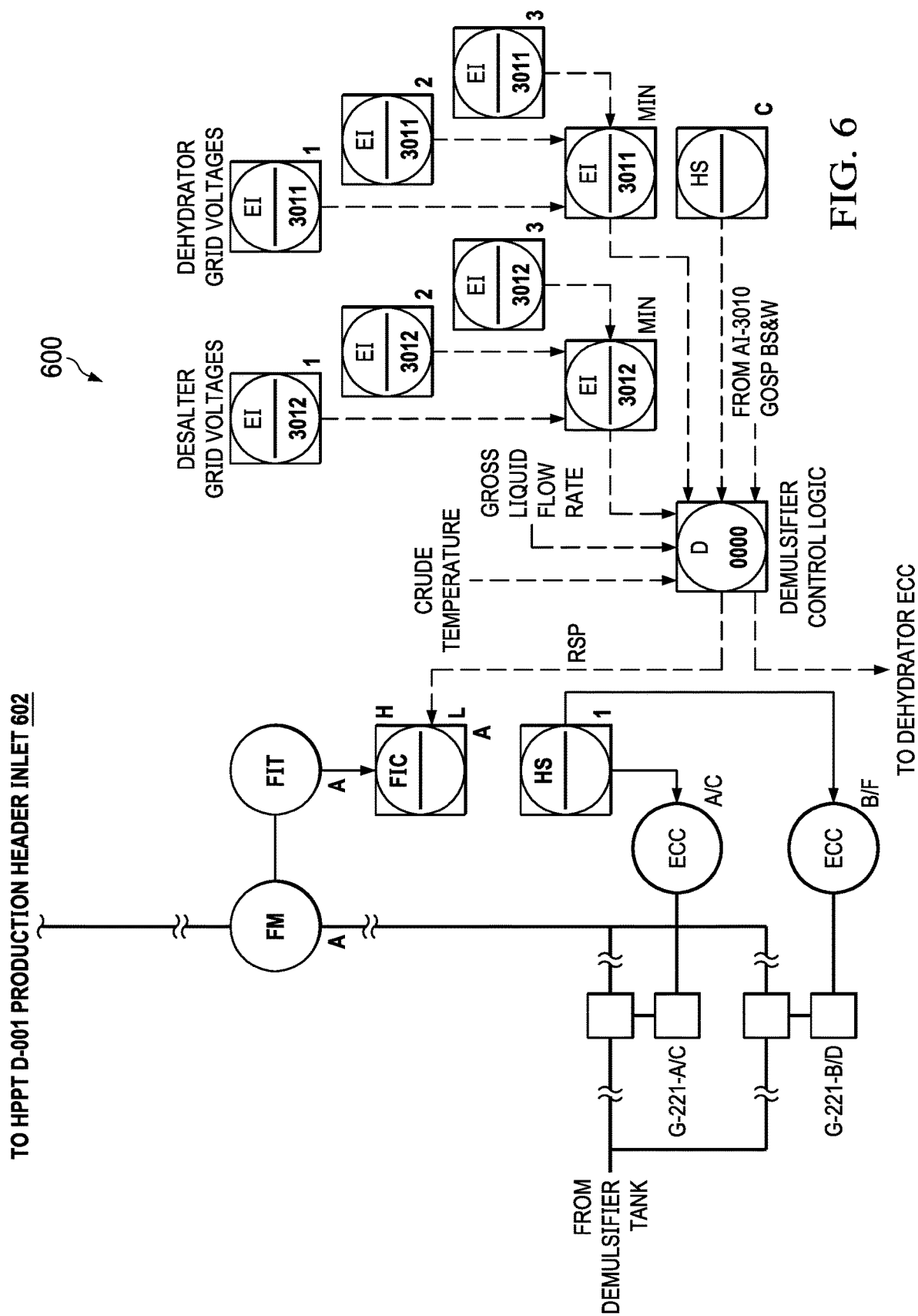
FIGS. 6-7 are schematic diagrams of examples of demulsifier automation templates for GOSPS, according to some implementations of the present disclosure.
Figure 7:
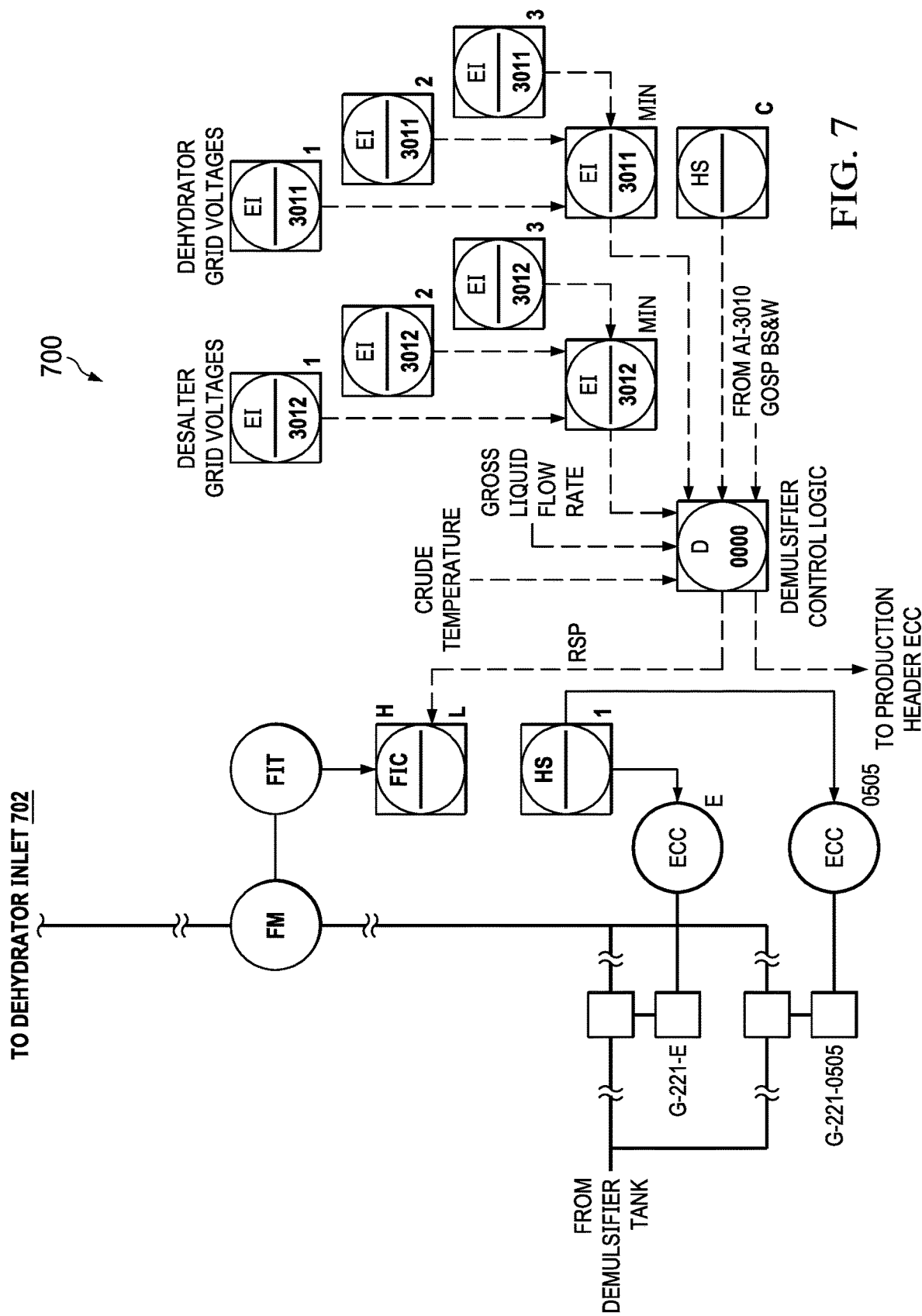

FIGS. 6-7 are schematic diagrams of examples of demulsifier automation templates 600 and 700 for GOSPs, according to some implementations of the present disclosure. The demulsifier automation template 600 includes a production header inlet 602. The demulsifier automation template 700 includes dehydrator inlet 702. The templates 600 and 700 can be developed for a distributed control system (DCS) that can provide a complete and proven rapid field execution capability.

Figure 8A:
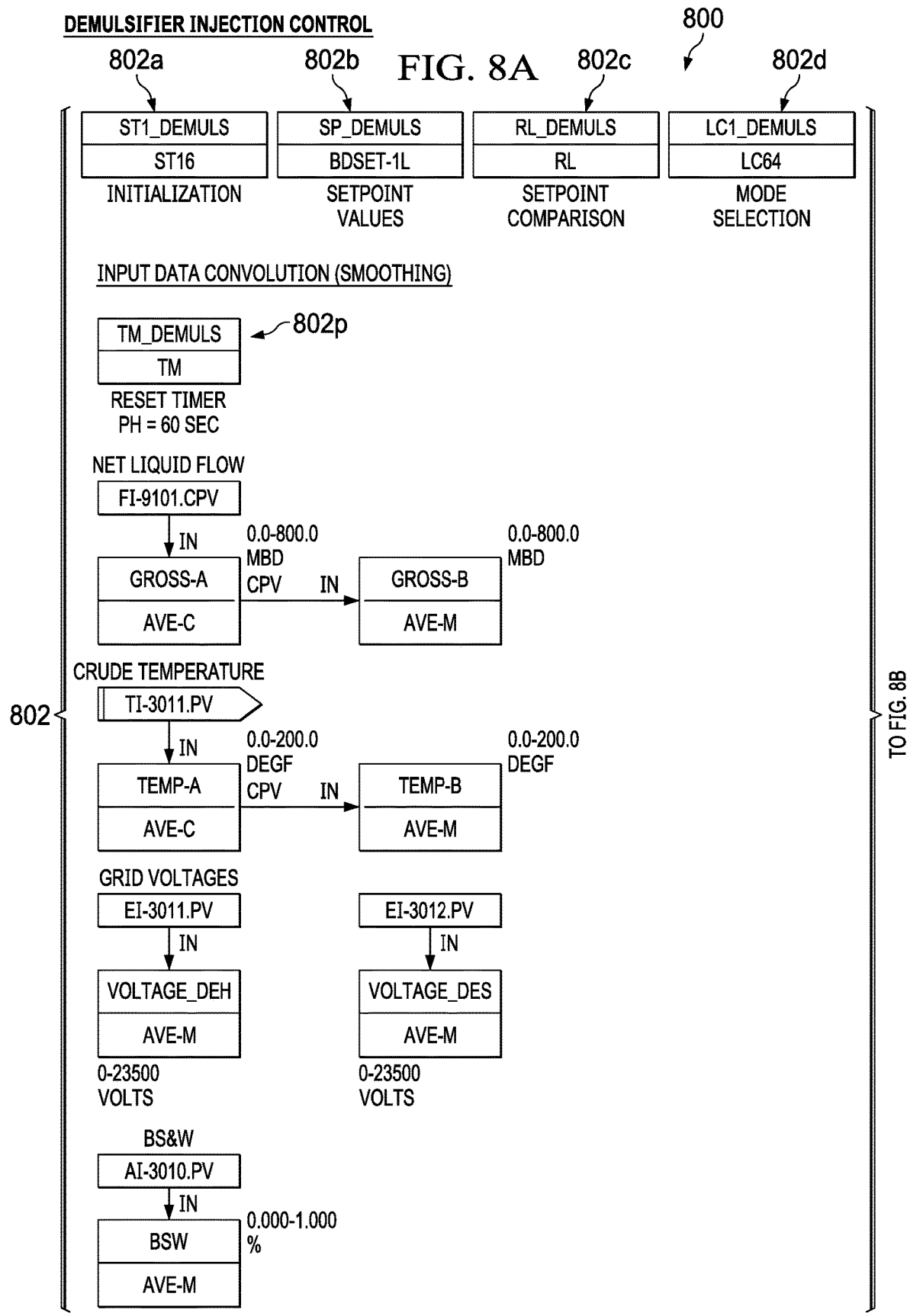
FIGS. 8A-8C are schematic diagrams collectively showing example controls and functions for demulsifier injection control, according to some implementations of the present disclosure.
Figure 8B:
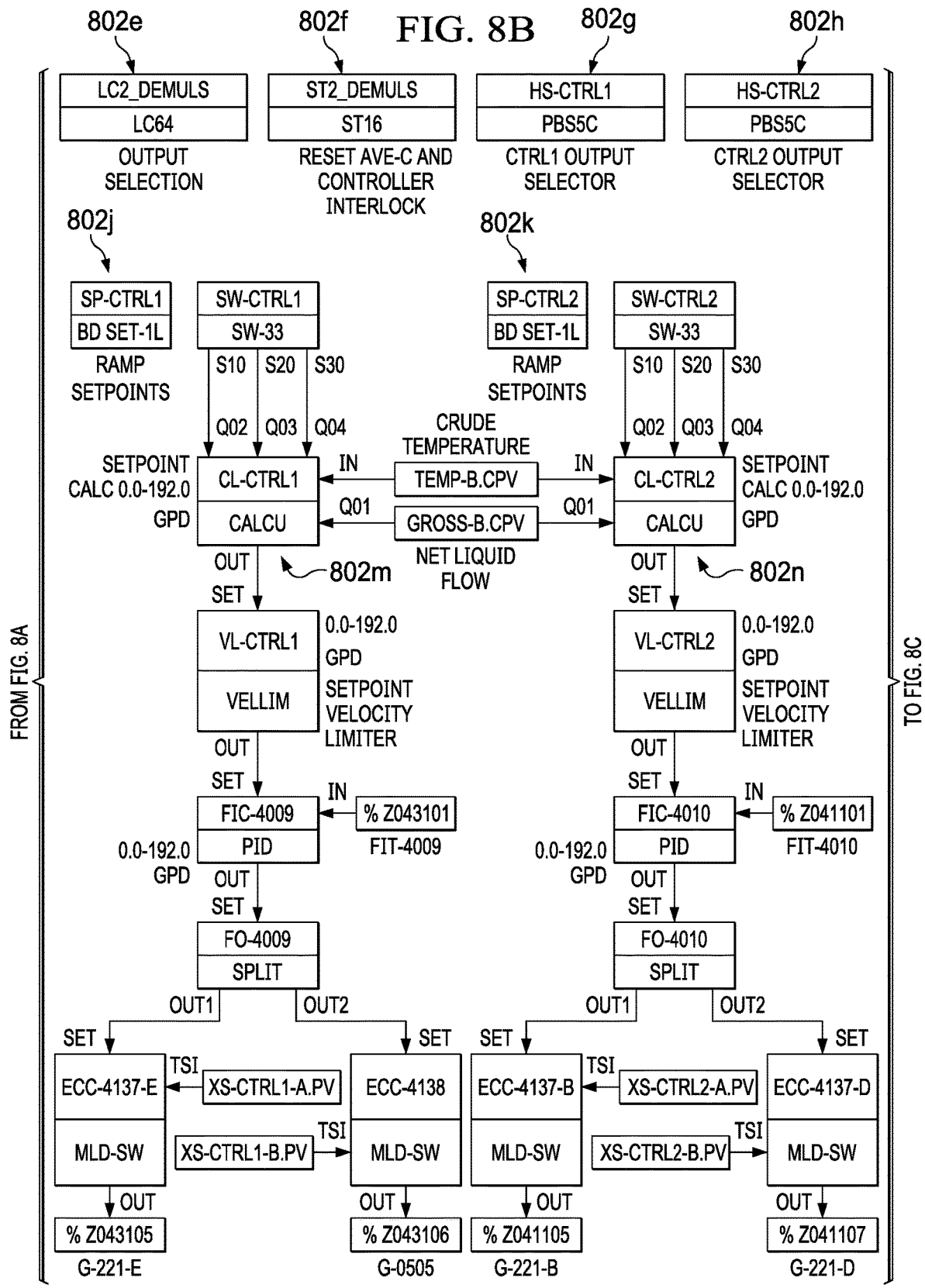
Figure 8C:
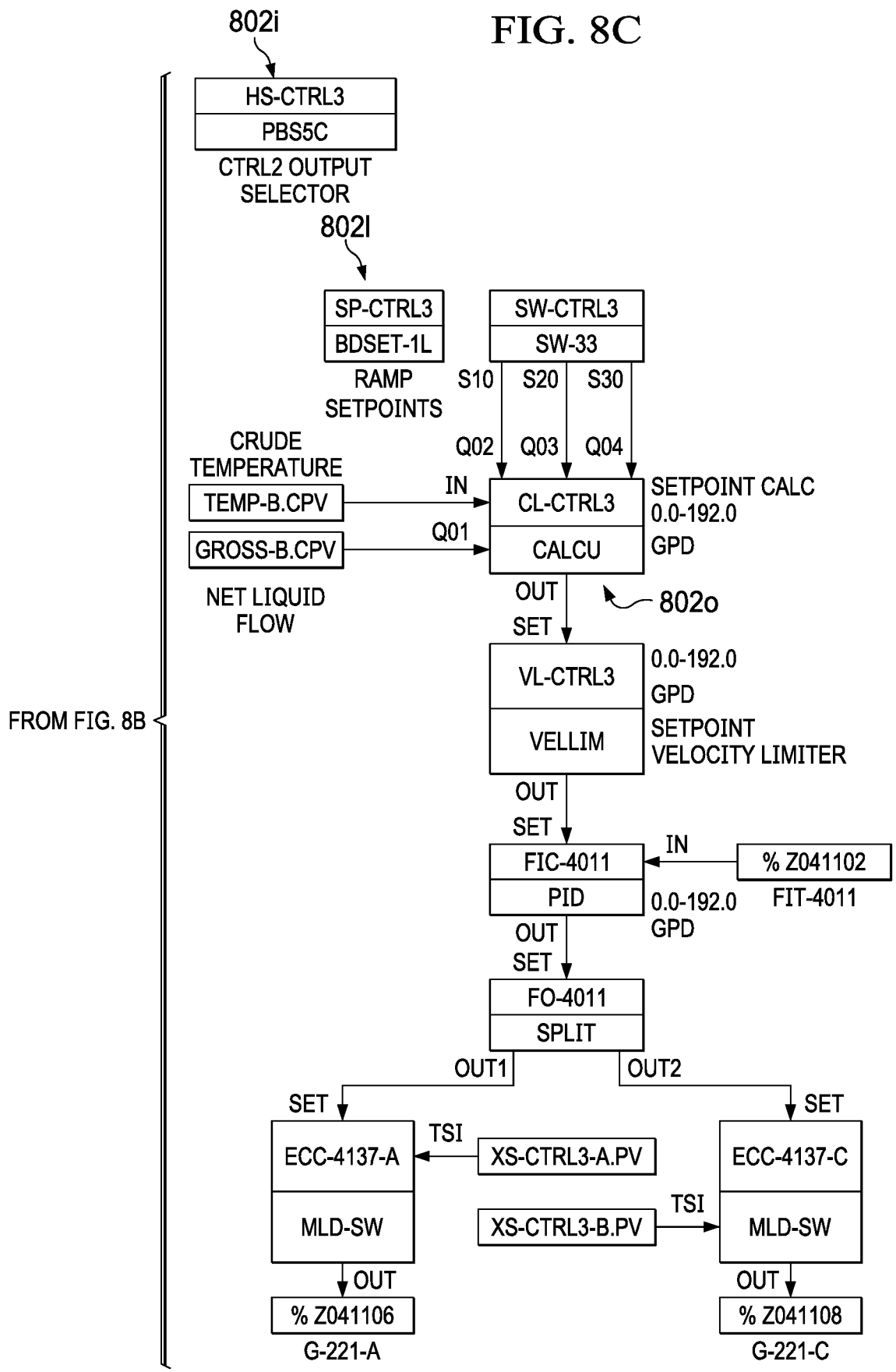

FIGS. 8A-8C are schematic diagrams collectively showing example controls and functions 802 for demulsifier injection control 800, according to some implementations of the present disclosure. Some of the controls and functions 802 (including functions 802a-802p) are listed and described in Table 2:

TABLE 2

Control Functions

| No | Function Block | Description |
|---|---|---|
| 802a | ST1_DEMULS | Initialization. Start up at initial cold start/restart. |
| 802b | SP-DEMULS | Setpoint constants for boundary conditions (trouble & normal) |
| 802c | RL-DEMULS | Setpoint comparison |
| 802d | LC1-DEMULS | Mode selection (Normal, Abnormal and Transit) |
| 802e | LC2-DEMULS | Output selection |
| 802f | ST2-DEMULS | Reset AVE-C (Yokogawa specific term) |
| 802g | HS-CTRL1 | Controller 1 output selector |
| 802h | HS-CTRL2 | Controller 2 output selector |
| 802i | HS-CTRL3 | Controller 3 output selector |
| 802j | SP-CTRL1 | Controller 1 ramp setpoints |
| 802k | SP-CTRL2 | Controller 2 ramp setpoints |
| 802l | SP-CTRL3 | Controller 3 ramp setpoints |
| 802m | CL-CTRL1 | Controller 1 setpoint calculations |
| 802n | CL-CTRL2 | Controller 2 setpoint calculations |
| 802o | CL-CTRL3 | Controller 3 setpoint calculations |
| 802p | TM_DEMULS | Reset timer |

Table 3 lists example boundary condition setpoint placeholders (trouble and normal) for function 802b:

TABLE 3

Boundary Conditions Setpoint Placeholders SP-DEMULS

| No | Parameter | UOM |
|---|---|---|
| 1. | Dehydrator Grid Trouble | VOLTS |
| 2. | Desalter Grid Trouble | VOLTS |
| 3. | BS&W Trouble | % |
| 4. | Dehydrator Grid Return to Normal | VOLTS |
| 5. | Desalter Grid Return to Normal | VOLTS |
| 6. | BS&W Return to Normal | % |

Table 4 lists example controller ramp setpoints, for example, for functions 802j-802l:

TABLE 4

Controller Ramp Setpoints SP-CTRL1, SP-CTRL2, SP-CTRL3

| No | Parameter | UOM | Remark |
|---|---|---|---|
| 1. | Multiply Factor—Normal | N/A | These values are typically the same |
| 2. | Multiply Factor—Transit | N/A | |

TABLE 4-continued

Controller Ramp Setpoints
SP-CTRL1, SP-CTRL2, SP-CTRL3

| No | Parameter | UOM | Remark |
|---|---|---|---|
| 3. | Multiply Factor—Abnormal | N/A | |
| 4. | DMVP (Increase Rate)—Normal | GPD/Scan | These values should always be |
| 5. | DMVP (Increase Rate)—Transit | GPD/Scan | the same. (DMVP = Yokogawa |
| 6. | DMVP (Increase Rate)—Abnormal | GPD/Scan | specific terms for Velocity limiter ramp up rate) |
| 7. | DMVM (Decrease Rate)—Normal | GPD/Scan | Equivalent to 60 gallons per hour reduction rate. (DMVM = Yokogawa specific terms for Velocity limiter ramp down rate) |
| 8. | DMVM (Decrease Rate)—Transit | GPD/Scan | These values should always be |
| 9. | DMVM (Decrease Rate)—Abnormal | GPD/Scan | the same |
| 10. | Transit Setpoint | GPD | VELLIM.DV threshold at which condition changes from Transit to Normal |
| 11. | Tracking Signal Input (TSI) | N/A | This is the value to drive the MLD blocks to when not selected by the operator. Should always be set to 0. |

In some implementations, a controller cascade (CAS) setpoint calculation can be given by:

$$PPM_{Target} = A \times e^{Bt} \quad (1)$$

where $PPM_{Target}$ is a target PPM of demulsifier to liquid flow, A is a demulsifier factor determined by a process, B is a demulsifier factor determined by a process, and t is a crude temperature (degrees Fahrenheit). Then, $PPM_{Target}$ can be used in:

$$SP_{CTRL1} = SF_{CTRL1} \times Q \times PPM_{Target} \quad (2)$$

$$SP_{CTRL2} = SF_{CTRL2} \times Q \times PPM_{Target} \quad (3)$$

where $SP_{CTRL1}$ is a cascade setpoint for production header flow controller, $SP_{CTRL2}$ is a cascade setpoint for dehydrator inlet flow controller, $SF_{CTRL}X$ is a multiply factor for respective cascade setpoint, and Q is a total liquid flow moving average value (in millions of barrels per day (MBD)).

Table 5 lists example calculation block parameters, for example, for functions 802m-802o:

TABLE 5

Calculation Block Parameters
CL-CTRL1, CL-CTRL2, CL-CTRL3

| No | Calculation Block Parameter | Parameter from Equations | Description |
|---|---|---|---|
| 1 | RV | T | Oil Temperature, degrees Fahrenheit |
| 2 | RV1 | Q | Total liquid Flow, MBD |
| 3 | RV2 | SFCTRLX | Multiply Factor |
| 4 | RV3 | N/A | VELUM DMVP |
| 5 | RV4 | N/A | VELUM DMVM |
| 6 | P01 | $e^{Bt}$ | Exponential factor |
| 7 | P02 | $PPM_{Target}$ | Target PPM for current temperature |
| 8 | P03 | $Q \times PPM_{Target}$ | Calculated setpoint of required demulsifier |
| 9 | P04 | SPCTRLX | Calculated setpoint including safety factor for Flow controller |
| 10 | CPV | SPCTRLX | Calculated setpoint including safety factor for Flow controller |
| 11 | CPV1 | N/A | Calculated value in GPD to switch from transit to Normal mode |

In some implementations, input data convolution and smoothening can be used as part of demulsifier automation. Selection of the sample interval or number of samples can be made to avoid absolute numbing of the data or having no smoothening effect at all. Techniques can include first figuring out what kind of frequencies are involved and then using engineering judgement to determine a suitable filter period, taking into account, for instance, the residence times in the separator vessels.

Figure 9:
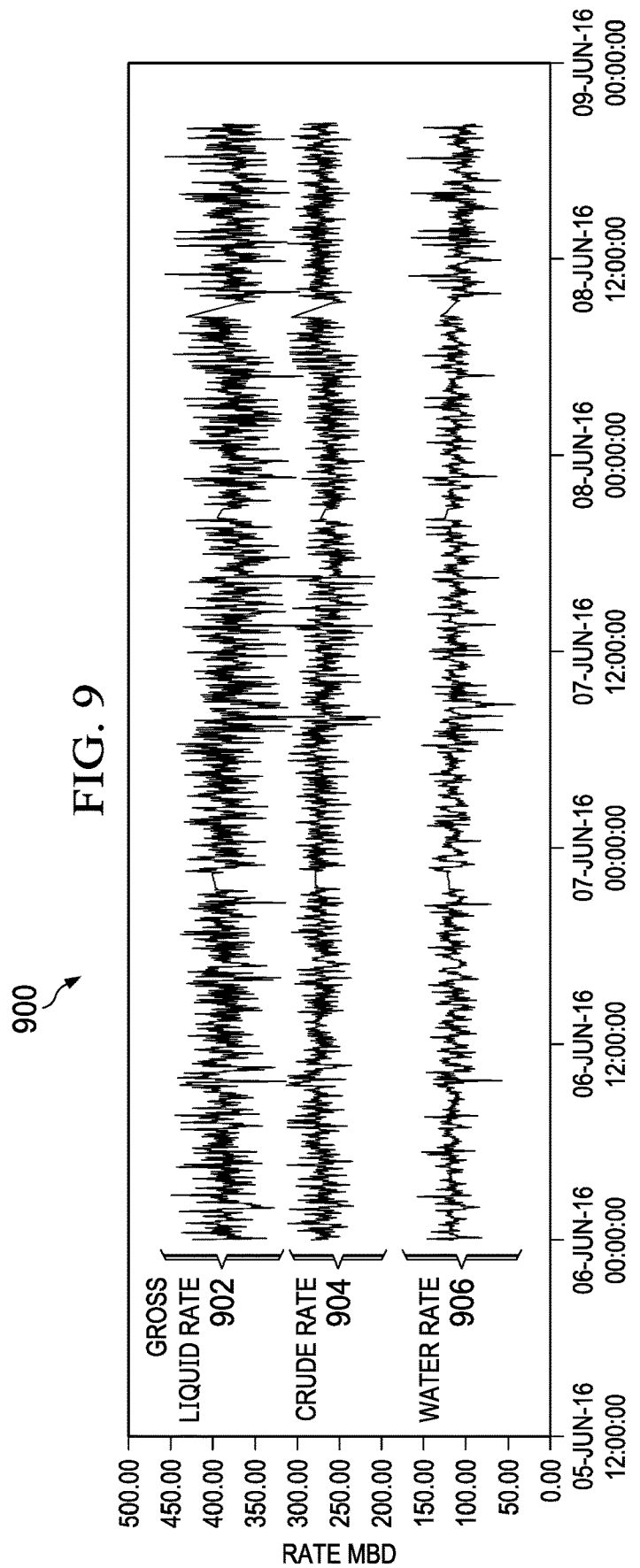
FIGS. 9, 10 are graphs showing examples of crude, water, and gross rates for a GOSP, according to some implementations of the present disclosure.
Figure 10:
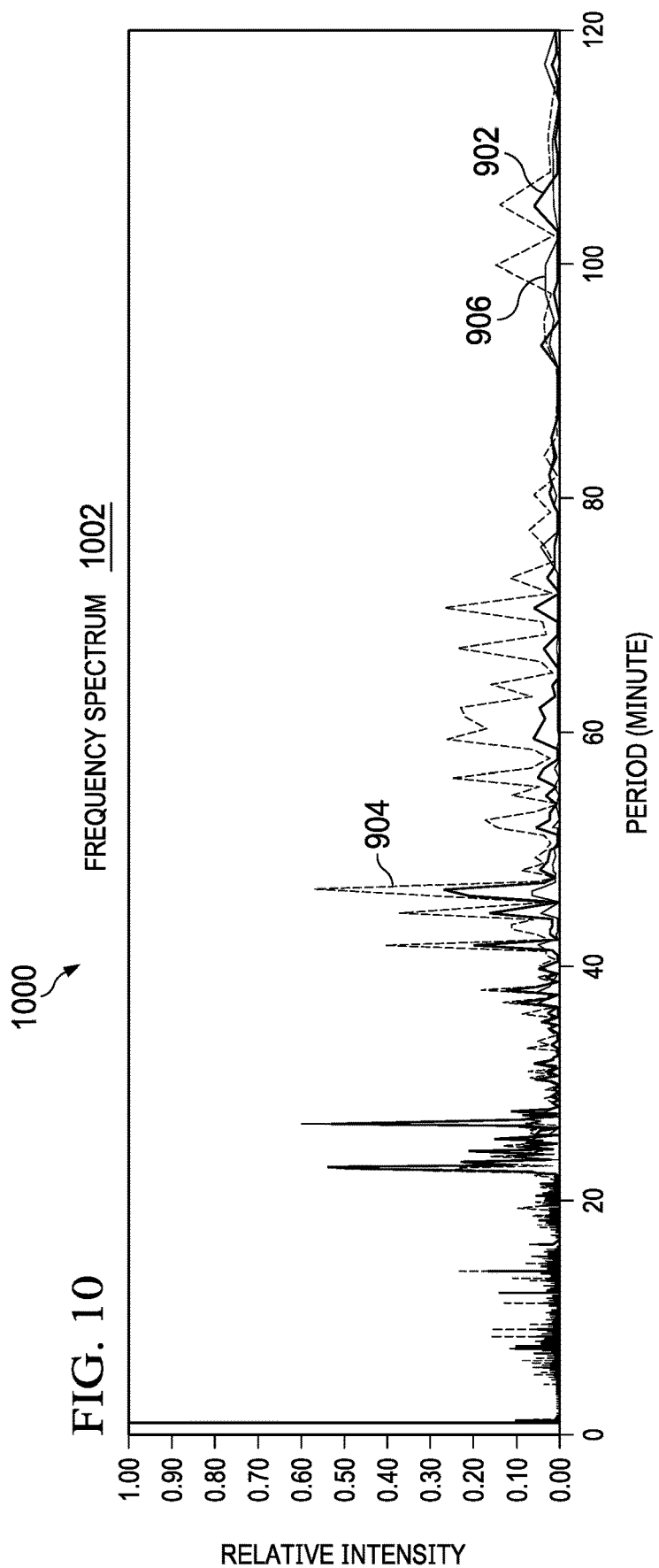

FIGS. 9, 10 are graphs 900, 1000 showing examples of a gross liquid rate 902, a net crude rate 904, and a net water rate 906 for a GOSP, according to some implementations of the present disclosure. For example, the rates 902-906 can correspond to a frequency spectrum (for example, using a Fourier transformation), resulting in two sine waves, in this particular example, each with a 45 MBD amplitude. Referring to FIG. 10, frequencies (or periods) 1002 for the net crude rate 904 and the gross liquid rate 902 can be quite different. In this particular example, the net crude rate 904, the strongest peaks can occur at 23 and 26 minutes, and for the gross liquid rate 902, the strongest peaks can occur at 42 and 47 minutes. The strongest peaks for the net water rate 906 can coincide with the water peaks at 23 and 26 minutes, where the net crude rate 904 is higher than the gross liquid rate 902. Any peak at a one-minute period can be considered to be trivial, such as when the dataset on which the analysis is based is sampled every minute. A relative intensity can be related to an amplitude of the fluctuation at a specific period, but the relative intensity cannot be used directly to obtain an amplitude in millions of barrels per day (MBD).

In this particular example for the demulsifier calculations, 23/26 minute variations can be filtered out. The total residence times of the liquid in the vessels can be greater than the 23/26 minute variations, so the vessels themselves can act, in a sense, as smoothing filters because there can be some degree of back-mixing in the vessels. Then, since the process itself smoothes things out, there is no need to adjust demulsifier rates more rapidly. Time periods can be rounded up to 30-minute intervals.

In some implementations, engineers can perform GOSP-specific Fourier transforms or other GOSP-specific calculations to determine dominant oscillation frequencies for liquid flow rates and the temperature for the particular GOSP for which the automation enhancement is implemented. Repeating this process for multiple GOSPs can facilitate the determination of values to use for a moving average block.

FIG. 11 is a graph 1100 of an example of a sine wave 1102, according to some implementations of the present disclosure. The sine wave 1102 can be based on the following values. A value t 1104 is a cumulative average interval time, for example, 60 seconds (sec). A value P is a sample period determined by Fourier Transform (in AVE-M block, P=SMPL×NUM). A value SMPL is a sample interval in seconds for AVE-M. The value NUM is a number of samples for AVE-M (for example, maximum=60).

Table 6 list example values for process variables that can be used for moving average blocks:

TABLE 6

Process Variables for Moving Average Blocks
Moving Average Blocks

| No | Process Variable | TAG | SMPL | NUM |
|----|------------------|-----|------|-----|
| 1 | Crude Temperature | TEMP-A | 60 sec | 60 |
| 2 | Total Liquid Flow | GROSS-A | 30 sec | 60 |
| 3 | Dehydrator Voltage | VOLTAGE-DEH | 1 sec | 60 |
| 4 | Desalter Voltage | VOLTAGE-DES | 1 sec | 60 |
| 5 | BS&W | BSW | 1 sec | 60 |

In some implementations, other controller enhancements and clean-up work for demulsifier automation design enhancement can include the following. In the event of any input failure or interruption of power (TOP), the flow controllers can switch to automatic mode, and the CAS mode can be disabled until the error is cleared. This is made possible because the calculation blocks CL-CTRL1 and CL-CTRL2 can be configured to revert to IOP when any of the inputs experience IOP (calculation input value error detected=all detection types). The logic chart LC2-DEMULS contains logic that, if the controller is in CAS mode and the calculation block has IOP, the controller is pulsed to AUTO mode. If the operator attempts to place the controller back in CAS, the logic chart will again pulse it back to AUTO. The last set value (SV) from the CAS signal will remain as the SV in AUTO mode.

In some implementations, output feedback tracking can be used. For example, an Operations group may normally have the ability to place the flow indicating controller (FIC) in any mode (for example, manual, automatic, or CAS) unless the pumps are not running. Because there are two pumps for each controller, the sequence table ST2-DEMULS can drive the controller pre-selected switch (PSW). In this scenario, if both pumps associated with the controller are not running, then the controller PSW can be operated. This can force the controller into manual mode and can drive the manipulated value (MV) to 0%. Example tags for sequence table logic are provided in Table 7:

TABLE 7

Tags for Sequence Table Logic

| Tag | Data | Description | Logic | |
|-----|------|-------------|-------|---|
| C1 | XL-PUMP1A.PV 1 | CTRL1 Pump A Run Status | N | |
| C2 | XL-PUMP1B.PV 1 | CTRL1 Pump B Run Status | N | |
| C3 | XL-PUMP2A.PV 1 | CTRL2 Pump A Run Status | | N |
| C4 | XL-PUMPB.PV 1 | CTRL2 Pump B Run Status | | N |
| A1 | FIC-CTRL1.PSW 1 | Force FIC to Manual, 0% MV | Y | |
| A2 | FIC-CTRL2.PSW 1 | Force FIC to Manual, 0% MV | | Y |

In some implementations, output selection logic can be used. For example, demulsifier logic can include operations that provide the ability to send controller output to either pump, or to both. To do this, a push button switch (PBS-5) can be provided for each controller. Three buttons can be provided to direct output to Pump A, to Pump B, or to both pumps, respectively. A transition between one output to another, which is preferred to be a smooth transition, can be done using the tracking signal input (TIN) and a tracking switch input (TSI). This logic can be controlled, for example, by function 802c (LC2-DEMULS). The tracking signal input can use a binary data set (BDSET) or storage array function block (for example, SP-CTRLX.DT11). For example, when the operator chooses to switch from Pump A to Pump B, the logic can actually switch from only sending the output to Pump A to sending the output to both Pump A and Pump B. When this happens, the output to Pump B can ramp up. After 30 seconds, a Pump A tracking switch can be, ramping its MV to 0%.

In the event that one of the pumps is not running, a selector switch can disable the respective Pump A or Pump B button (as well as the "BOTH" button). Disabling can be done by the ST2-DEMULS sequence table.

Figure 12A:
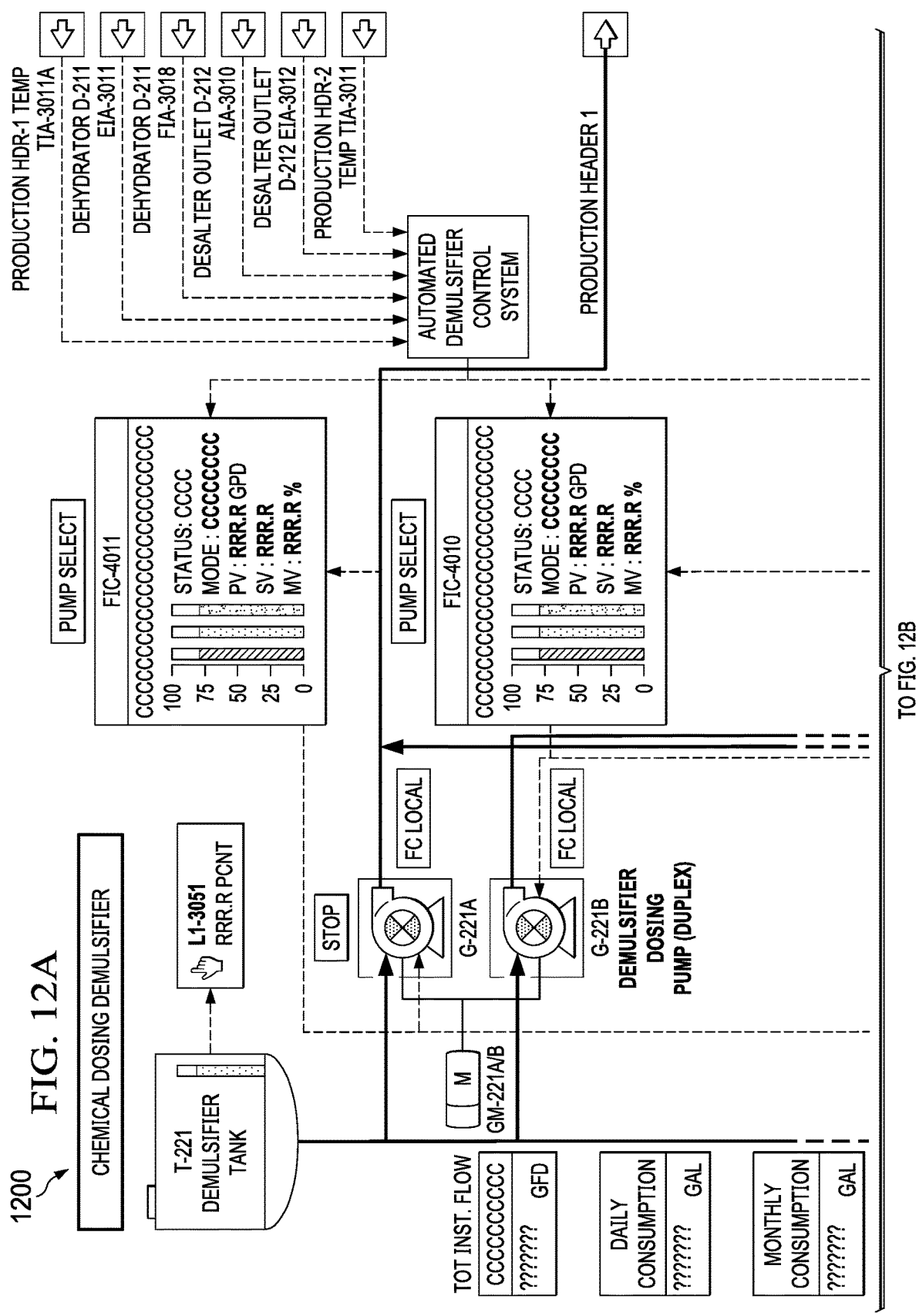
FIGS. 12A-12B are schematic diagrams collectively showing an example of a chemical dosing demulsifier, according to some implementations of the present disclosure.
Figure 12B:
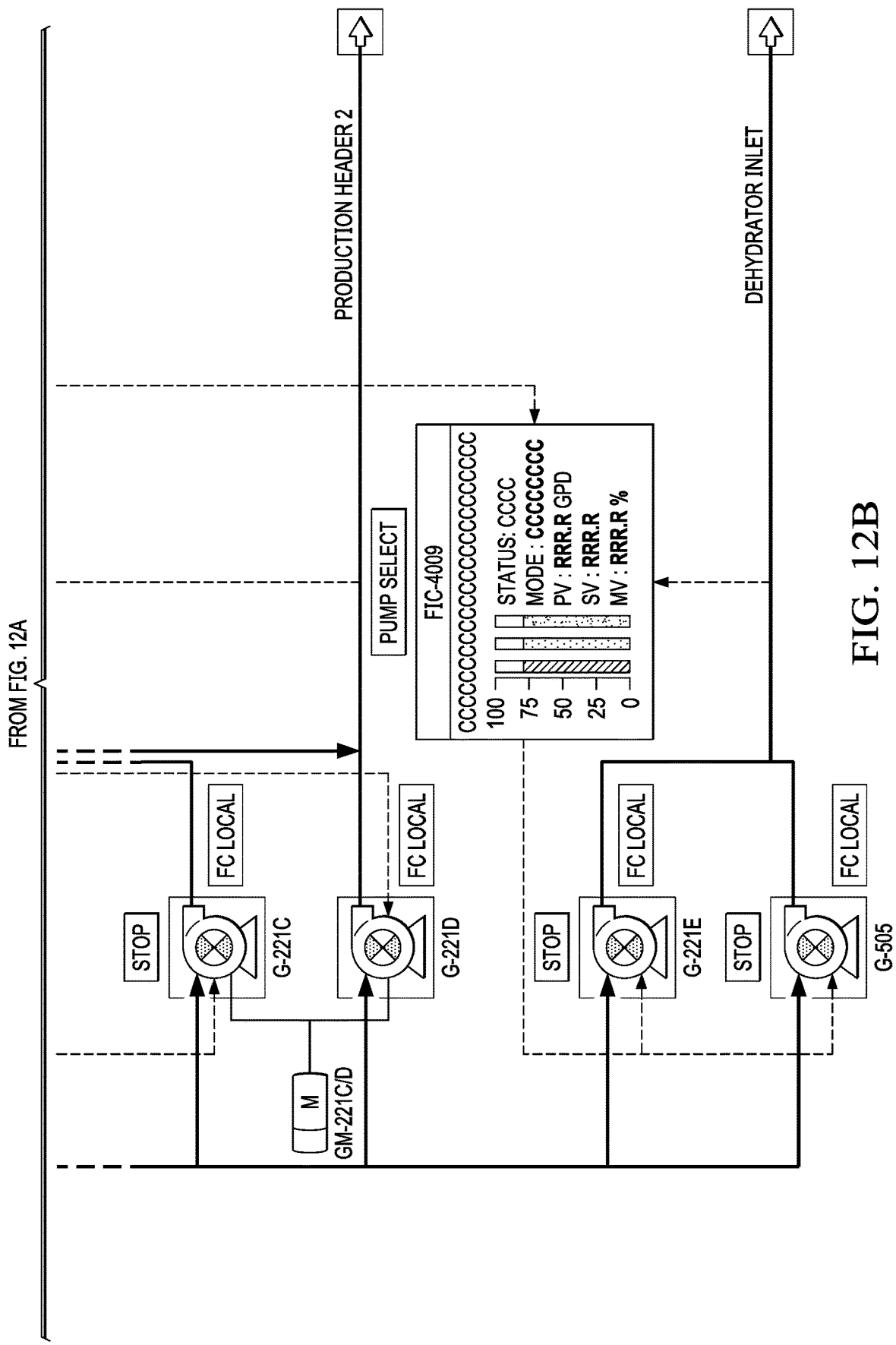

FIGS. 12A-12B are schematic diagrams collectively showing an example of a chemical dosing demulsifier 1200, according to some implementations of the present disclosure.

Figure 13A:
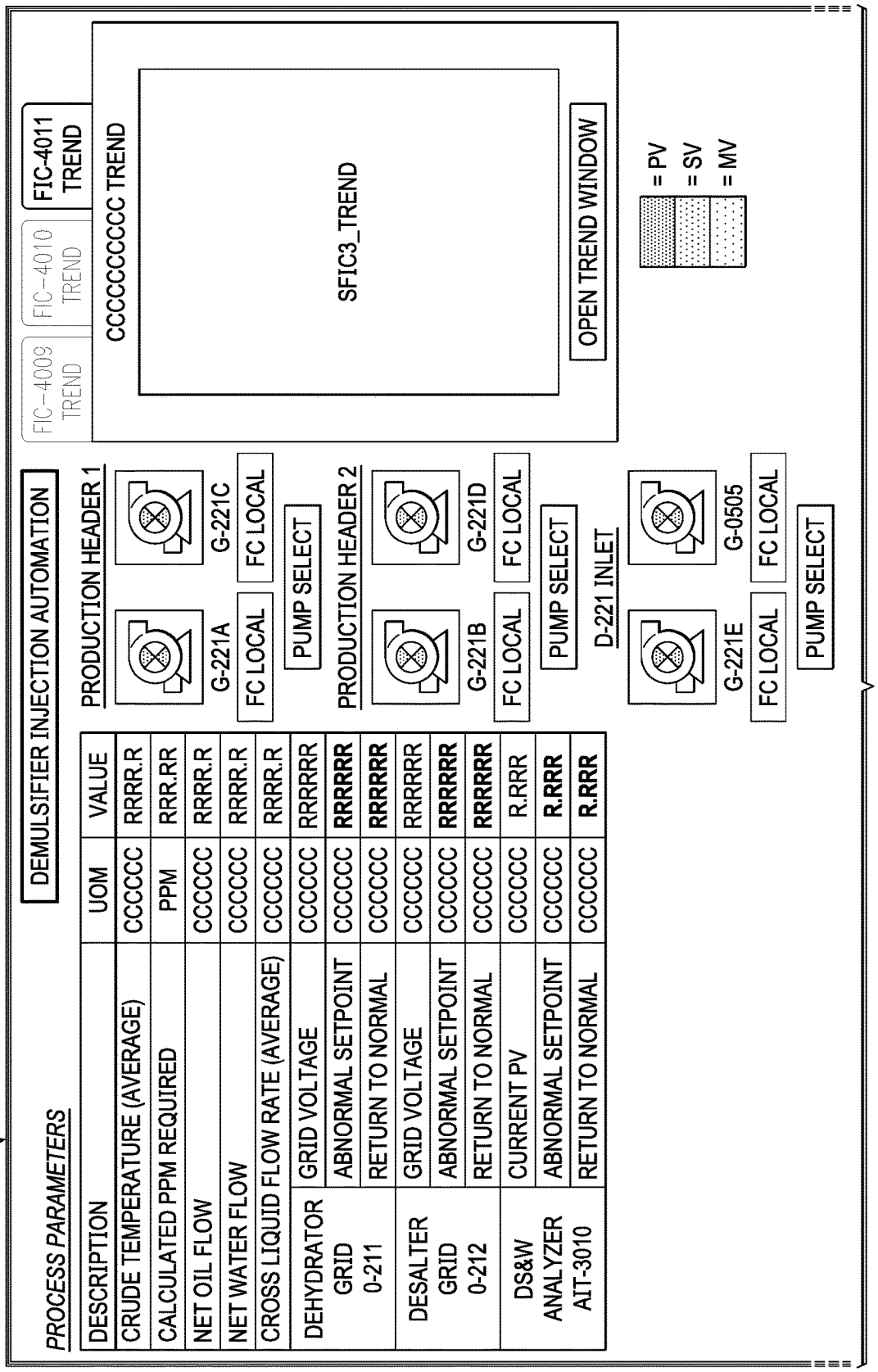

FIGS. 13A-13B collectively show a screen print of an example of an operator interface 1300 for demulsifier injection automation, according to some implementations of the present disclosure. For example, an operator can use the operator interface 1300 to select which pump to run, manipulate the control action (for example, manual, automatic, or CAS). In some implementations, the operator interface 1300 can be provided on a controller faceplate of equipment that is used at a GOSP.

The operator interface 1300 can include a demulsifier injection automation page that allows the operator to view information and/or control process input parameter smoothening, perform calculation of the demulsifier PPM rate and injection rates, view demulsifier control status, view status of the chemical injection pumps, and view trends for monitoring controller performance.

FIGS. 14A-14B collectively show a screen print of an example of an engineering parameter entry interface 1400, according to some implementations of the present disclosure. The engineering parameter entry interface 1400 can provide an engineer, for example, with an overview of various input parameters and controller settings for the different operational states (for example, normal, abnormal and transit). Based at least on the provided information, the engineer can use the engineering parameter entry interface 1400 to adjust initial margins (similar to a surge control line) during the initial implementation. For example, upon the calculation and presentation of real-time performance indicators, the engineer can see whether the target PPM curves need to be calibrated. In some implementations, the ability to change parameters can be limited to users who have engineering privilege.

In some implementations, demulsifier performance curves can be programmed to determine required dosing rates based on temperature and total liquid rates. Implementation can occur in existing band-based demulsifier logic as the first band, which is normal operation.

In some implementations, the results achieved through demulsifier automation optimization and control can be further improved using other techniques. For example, interface levels can be maintained to match the Operations Instruction Manual (OIM). Dehydrator operating levels can be set by the designer to establish enough space between the interface level and the lower transformer grids to avoid getting more water droplets into the oil phase, which can increase the conductivity and result in low transformers voltage.

In some implementations, weekly jetting and skimming can be performed on the dehydrator and desalter. This can assure frequent removal of the emulsion layer, which can help to avoid transformer low voltages due to an accumulation of water droplets into the oil phase.

In some implementations, an interface layer washout can be performed regularly (for example, quarterly). For example, the interface zone may contain one or more of solids, hydrocarbon films, and other polymeric compounds. This can lead to a build-up of a "rag" layer at the interface zone that can significantly reduce the migration of separated water to the water phase at the bottom of the vessel. Washing out of the "rag" layer can improve the water separation in high pressure production traps (HPPTs).

In some implementations, various techniques can be used to identify when overdosing of the demulsifier is occurring. Demulsifier overdosing can result in enhanced stability of the emulsion, leading to "rag" layers or pads inside the separators. This can be a problem that can worsen with increased demulsifier costs.

In some implementations, the demulsifier quality can be continuously reviewed and enhanced to ensure effective performance. This can be firmly applied during the phase-in of new chemicals. In some implementations, it can be assured that all associated instrumentation in the field are maintained and in good operational condition.

In some implementations, a periodic program can be used to review demulsifier control settings. The program can be implemented to verify, for example, that step response multiplication factors and ramp-down rates are still relevant. Process upsets can be corrected by the logic as quickly as possible to assure crude quality.

Figure 15:
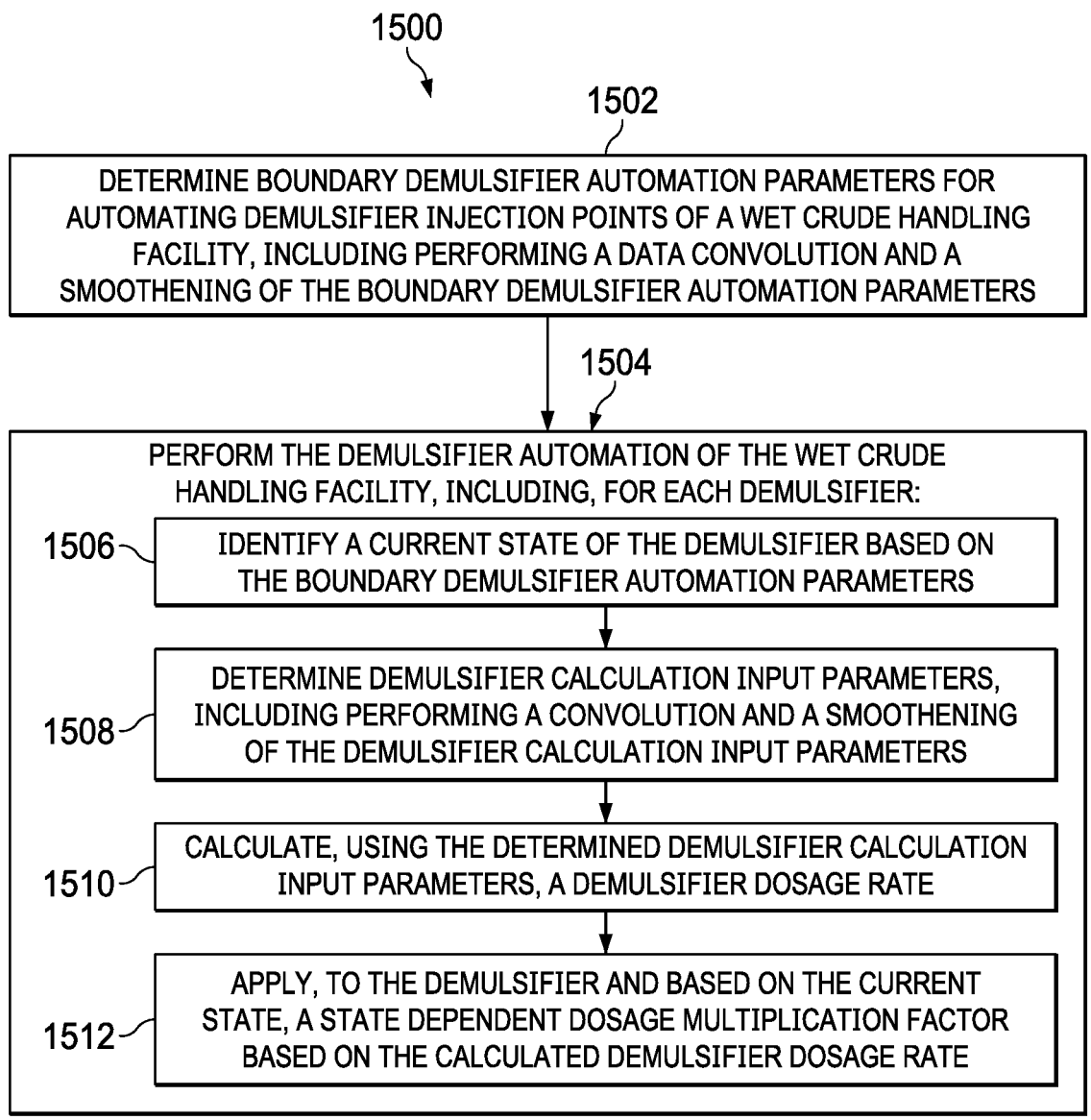
FIG. 15 is a flowchart of an example method for automating demulsifier flow rates, according to some implementations of the present disclosure.

FIG. 15 is a flowchart of an example method 1500 for automating demulsifier flow rates, according to some implementations of the present disclosure. For clarity of presentation, the description that follows generally describes method 1500 in the context of the other figures in this description. However, it will be understood that method 1500 may be performed, for example, by any suitable system, environment, software, and hardware, or a combination of systems, environments, software, and hardware, as appropriate. In some implementations, various steps of method 1500 can be run in parallel, in combination, in loops, or in any order.

At 1502, demulsifier automation parameters are determined for automating demulsifier injection points of a wet crude handling facility, the determining including performing a data convolution and a smoothening of inlet demulsifier automation parameters. For example, demulsifier automation parameters related to temperature, dehydrator voltages, desalter voltages, dehydrator water outlet flow rates, and BS&W at a desalter outlet can be determined for the wet crude handling facility 100. From 1502, method 1500 proceeds to 1504.

At 1504, the demulsifier automation of the wet crude handling facility is performed, including, for each demulsifier. For example, demulsifiers for the wet crude handling facility 100 can be automated according to steps 1506 through 1512.

At 1506, a current state of the demulsifier is identified based on the demulsifier automation parameters. For example, a the current state of a given demulsifier of the wet crude handling facility 100 can be one of the states identified with respect to FIG. 2. States of the demulsifier can include a normal state, an abnormal state, and a transit state. From 1506, method 1500 proceeds to 1508.

At 1508, demulsifier calculation input parameters are determined, including performing a convolution and a smoothening of the demulsifier calculation input parameters. For example, changes can be made in one or both of sampling intervals and number of samples in order to make the parameter more stable. In some implementations, the input parameters can include a crude temperature and a GOSP total liquid flowrate. In some implementations, the GOSP total liquid flowrate is a sum of a net crude export rate and a net water injection rate. From 1508, method 1500 proceeds to 1510.

At 1510, a demulsifier dosage rate is calculated using the determined demulsifier calculation input parameters. For example, the demulsifier dosage rate calculation 401 can be determined as described with reference to FIG. 4. From 1510, method 1500 proceeds to 1512.

At 1512 a state dependent dosage multiplication factor is applied to the demulsifier based on the current state and calculated demulsifier dosage rate. As an example, each demulsifier in can be adjusted based on determined state dependent dosage multiplication factors. After 1512, method 1500 stops.

Figure 16:
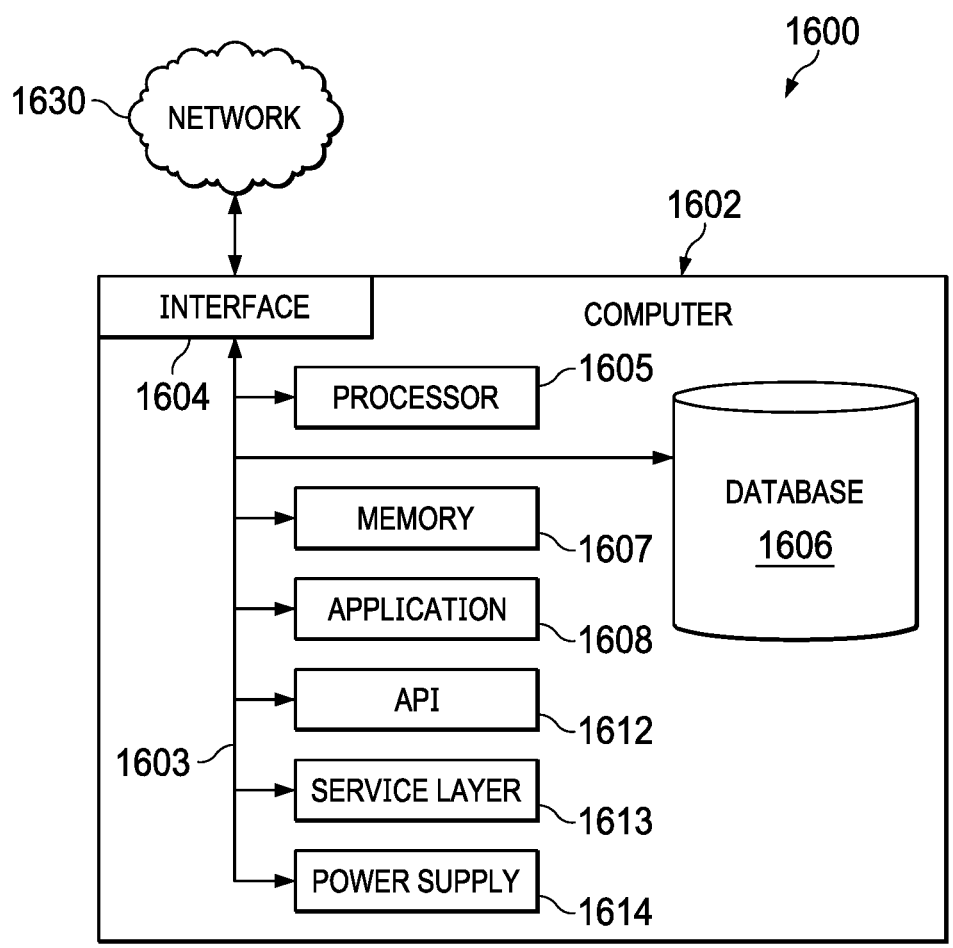
FIG. 16 is a block diagram of an example computer system used to provide computational functionalities associated with described algorithms, methods, functions, processes, flows, and procedures, as described in the instant disclosure, according to some implementations of the present disclosure.

FIG. 16 is a block diagram of an example computer system 1600 used to provide computational functionalities associated with described algorithms, methods, functions, processes, flows, and procedures, as described in the instant disclosure, according to some implementations of the present disclosure. The illustrated computer 1602 is intended to encompass any computing device such as a server, desktop computer, laptop/notebook computer, wireless data port, smart phone, personal data assistant (PDA), tablet computing device, one or more processors within these devices, or any other suitable processing device, including physical or virtual instances (or both) of the computing device. Additionally, the computer 1602 may comprise a computer that includes an input device, such as a keypad, keyboard, touch screen, or other device that can accept user information, and an output device that conveys information associated with the operation of the computer 1602, including digital data, visual, or audio information (or a combination of information), or a graphical-type user interface (UI) (or GUI).

The computer 1602 can serve in a role as a client, network component, a server, a database or other persistency, or any other component (or a combination of roles) of a computer system for performing the subject matter described in the instant disclosure. The illustrated computer 1602 is communicably coupled with a network 1630. In some implementations, one or more components of the computer 1602 may be configured to operate within environments, including cloud-computing-based, local, global, or other environment (or a combination of environments).

At a high level, the computer 1602 is an electronic computing device operable to receive, transmit, process, store, or manage data and information associated with the described subject matter. According to some implementations, the computer 1602 may also include or be communicably coupled with an application server, e-mail server, web server, caching server, streaming data server, or other server (or a combination of servers).

The computer 1602 can receive requests over network 1630 from a client application (for example, executing on another computer 1602) and respond to the received requests by processing the received requests using an appropriate software application(s). In addition, requests may also be sent to the computer 1602 from internal users (for example, from a command console or by other appropriate access method), external or third-parties, other automated applications, as well as any other appropriate entities, individuals, systems, or computers.

Each of the components of the computer 1602 can communicate using a system bus 1603. In some implementations, any or all of the components of the computer 1602, hardware or software (or a combination of both hardware and software), may interface with each other or the interface 1604 (or a combination of both), over the system bus 1603 using an application programming interface (API) 1612 or a service layer 1613 (or a combination of the API 1612 and service layer 1613). The API 1612 may include specifications for routines, data structures, and object classes. The API 1612 may be either computer-language independent or dependent and refer to a complete interface, a single function, or even a set of APIs. The service layer 1613 provides software services to the computer 1602 or other components (whether or not illustrated) that are communicably coupled to the computer 1602. The functionality of the computer 1602 may be accessible for all service consumers using this service layer. Software services, such as those provided by the service layer 1613, provide reusable, defined functionalities through a defined interface. For example, the interface may be software written in JAVA, C++, or other suitable language providing data in extensible markup language (XML) format or other suitable format. While illustrated as an integrated component of the computer 1602, alternative implementations may illustrate the API 1612 or the service layer 1613 as stand-alone components in relation to other components of the computer 1602 or other components (whether or not illustrated) that are communicably coupled to the computer 1602. Moreover, any or all parts of the API 1612 or the service layer 1613 may be implemented as child or sub-modules of another software module, enterprise application, or hardware module without departing from the scope of this disclosure.

The computer 1602 includes an interface 1604. Although illustrated as a single interface 1604 in FIG. 16, two or more interfaces 1604 may be used according to particular needs, desires, or particular implementations of the computer 1602. The interface 1604 is used by the computer 1602 for communicating with other systems that are connected to the network 1630 (whether illustrated or not) in a distributed environment. Generally, the interface 1604 comprises logic encoded in software or hardware (or a combination of software and hardware) and is operable to communicate with the network 1630. More specifically, the interface 1604 may comprise software supporting one or more communication protocols associated with communications such that the network 1630 or interface's hardware is operable to communicate physical signals within and outside of the illustrated computer 1602.

The computer 1602 includes a processor 1605. Although illustrated as a single processor 1605 in FIG. 16, two or more processors may be used according to particular needs, desires, or particular implementations of the computer 1602. Generally, the processor 1605 executes instructions and manipulates data to perform the operations of the computer 1602 and any algorithms, methods, functions, processes, flows, and procedures as described in the instant disclosure.

The computer 1602 also includes a database 1606 that can hold data for the computer 1602 or other components (or a combination of both) that can be connected to the network 1630 (whether illustrated or not). For example, database 1606 can be an in-memory, conventional, or other type of database storing data consistent with this disclosure. In some implementations, database 1606 can be a combination of two or more different database types (for example, a hybrid in-memory and conventional database) according to particular needs, desires, or particular implementations of the computer 1602 and the described functionality. Although illustrated as a single database 1606 in FIG. 16, two or more databases (of the same or combination of types) can be used according to particular needs, desires, or particular implementations of the computer 1602 and the described functionality. While database 1606 is illustrated as an integral component of the computer 1602, in alternative implementations, database 1606 can be external to the computer 1602.

The computer 1602 also includes a memory 1607 that can hold data for the computer 1602 or other components (or a combination of both) that can be connected to the network 1630 (whether illustrated or not). Memory 1607 can store any data consistent with this disclosure. In some implementations, memory 1607 can be a combination of two or more different types of memory (for example, a combination of semiconductor and magnetic storage) according to particular needs, desires, or particular implementations of the computer 1602 and the described functionality. Although illustrated as a single memory 1607 in FIG. 16, two or more memories 1607 (of the same or combination of types) can be used according to particular needs, desires, or particular implementations of the computer 1602 and the described functionality. While memory 1607 is illustrated as an integral component of the computer 1602, in alternative implementations, memory 1607 can be external to the computer 1602.

The application 1608 is an algorithmic software engine providing functionality according to particular needs, desires, or particular implementations of the computer 1602, particularly with respect to functionality described in this disclosure. For example, application 1608 can serve as one or more components, modules, or applications. Further, although illustrated as a single application 1608, the application 1608 may be implemented as multiple applications 1608 on the computer 1602. In addition, although illustrated as integral to the computer 1602, in alternative implementations, the application 1608 can be external to the computer 1602.

The computer 1602 can also include a power supply 1614. The power supply 1614 can include a rechargeable or non-rechargeable battery that can be configured to be either user- or non-user-replaceable. In some implementations, the power supply 1614 can include power-conversion or management circuits (including recharging, standby, or other power management functionality). In some implementations, the power-supply 1614 can include a power plug to allow the computer 1602 to be plugged into a wall socket or other power source to, for example, power the computer 1602 or recharge a rechargeable battery.

There may be any number of computers 1602 associated with, or external to, a computer system containing computer 1602, each computer 1602 communicating over network 1630. Further, the term "client," "user," and other appropriate terminology may be used interchangeably, as appropriate, without departing from the scope of this disclosure. Moreover, this disclosure contemplates that many users may use one computer 1602, or that one user may use multiple computers 1602.

Described implementations of the subject matter can include one or more features, alone or in combination.

For example, in a first implementation, a computer-implemented method, comprising: determining demulsifier automation parameters for automating demulsifier injection points of a wet crude handling facility, the determining including performing a data convolution and a smoothening of inlet demulsifier automation parameters; and performing the demulsifier automation of the wet crude handling facility, including, for each demulsifier: identifying a current state of the demulsifier, the identifying based on the demulsifier automation parameters; determining demulsifier calculation input parameters, including performing a convolution and a smoothening of the demulsifier calculation input parameters; calculating, using the determined demulsifier calculation input parameters, a demulsifier dosage rate; applying, to the demulsifier and based on the current state, a state dependent dosage multiplication factor based on the calculated demulsifier dosage rate.

The foregoing and other described implementations can each, optionally, include one or more of the following features:

A first feature, combinable with any of the following features, the method further comprising: wherein states of the demulsifier include a normal state, an abnormal state, and a transit state.

A second feature, combinable with any of the previous or following features, further comprising performing a state transition from the current state to a new state based on the current state and a determination that a boundary condition has been breached or, when the current state is the transit state, has become normalized.

A third feature, combinable with any of the previous or following features, wherein state transitions are state-dependent and include: a state transition from the normal state to the abnormal state when the boundary condition is breached; a state transition from the transit state to the abnormal state when the boundary condition is breached; a state transition from the abnormal state to the transit state when the boundary condition is normalized; and a state transition from the transit state to the normal state when the boundary condition and the transit setpoint are normal.

A fourth feature, combinable with any of the previous or following features, wherein, when the current state is the abnormal state, transitioning to the normal state cannot occur without first transitioning to the transit state.

A fifth feature, combinable with any of the previous or following features, wherein the input parameters include a crude temperature and a GOSP total liquid flowrate.

A sixth feature, combinable with any of the previous or following features, wherein the GOSP total liquid flowrate is a sum of a net crude export rate and a net water injection rate.

A seventh feature, combinable with any of the previous or following features, wherein the boundary conditions include threshold values for a temperature, a dehydrator voltage, a desalter voltage, a dehydrator water outlet flow, and a basic sediment and water (BS&W) at a desalter outlet.

In a second implementation, a non-transitory, computer-readable medium storing one or more instructions executable by a computer system to perform operations comprising: determining demulsifier automation parameters for automating demulsifier injection points of a wet crude handling facility, the determining including performing a data convolution and a smoothening of inlet demulsifier automation parameters; and performing the demulsifier automation of the wet crude handling facility, including, for each demulsifier: identifying a current state of the demulsifier, the identifying based on the demulsifier automation parameters; determining demulsifier calculation input parameters, including performing a convolution and a smoothening of the demulsifier calculation input parameters; calculating, using the determined demulsifier calculation input parameters, a demulsifier dosage rate; applying, to the demulsifier and based on the current state, a state dependent dosage multiplication factor based on the calculated demulsifier dosage rate.

The foregoing and other described implementations can each, optionally, include one or more of the following features:

A first feature, combinable with any of the following features, the method further comprising: wherein states of the demulsifier include a normal state, an abnormal state, and a transit state.

A second feature, combinable with any of the previous or following features, the operations further comprising performing a state transition from the current state to a new state based on the current state and a determination that a boundary condition has been breached or, when the current state is the transit state, has become normalized.

A third feature, combinable with any of the previous or following features, wherein state transitions are state-dependent and include: a state transition from the normal state to the abnormal state when the boundary condition is breached; a state transition from the transit state to the abnormal state when the boundary condition is breached; a state transition from the abnormal state to the transit state when the boundary condition is normalized; and a state transition from the transit state to the normal state when the boundary condition and the transit setpoint are normal.

A fourth feature, combinable with any of the previous or following features, wherein, when the current state is the abnormal state, transitioning to the normal state cannot occur without first transitioning to the transit state.

A fifth feature, combinable with any of the previous or following features, wherein the input parameters include a crude temperature and a GOSP total liquid flowrate.

A sixth feature, combinable with any of the previous or following features, wherein the GOSP total liquid flowrate is a sum of a net crude export rate and a net water injection rate.

A seventh feature, combinable with any of the previous or following features, wherein the boundary conditions include threshold values for a temperature, a dehydrator voltage, a desalter voltage, a dehydrator water outlet flow, and a basic sediment and water (BS&W) at a desalter outlet.

In a third implementation, a computer-implemented system, comprising a computer memory; and a hardware processor interoperably coupled with the computer memory and configured to perform operations comprising: determining demulsifier automation parameters for automating demulsifier injection points of a wet crude handling facility, the determining including performing a data convolution and a smoothening of inlet demulsifier automation parameters; and performing the demulsifier automation of the wet crude handling facility, including, for each demulsifier: identifying a current state of the demulsifier, the identifying based on the demulsifier automation parameters; determining demulsifier calculation input parameters, including performing a convolution and a smoothening of the demulsifier calculation input parameters; calculating, using the determined demulsifier calculation input parameters, a demulsifier dosage rate; applying, to the demulsifier and based on the current state, a state dependent dosage multiplication factor based on the calculated demulsifier dosage rate.

The foregoing and other described implementations can each, optionally, include one or more of the following features:

A first feature, combinable with any of the following features, the method further comprising: wherein states of the demulsifier include a normal state, an abnormal state, and a transit state.

A second feature, combinable with any of the previous or following features, the operations further comprising performing a state transition from the current state to a new state based on the current state and a determination that a boundary condition has been breached or, when the current state is the transit state, has become normalized.

A third feature, combinable with any of the previous or following features, wherein state transitions are state-dependent and include: a state transition from the normal state to the abnormal state when the boundary condition is breached; a state transition from the transit state to the abnormal state when the boundary condition is breached; a state transition from the abnormal state to the transit state when the boundary condition is normalized; and a state transition from the transit state to the normal state when the boundary condition and the transit setpoint are normal.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs, that is, one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal, for example, a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be, or further include special purpose logic circuitry, for example, a central processing unit (CPU), a field programmable gate array (FPGA), or an application-specific integrated circuit (ASIC). In some implementations, the data processing apparatus or special purpose logic circuitry (or a combination of the data processing apparatus or special purpose logic circuitry) may be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example LINUX, UNIX, WINDOWS, MAC OS, ANDROID, IOS, or any other suitable conventional operating system.

A computer program, which may also be referred to or described as a program, software, a software application, a module, a software module, a script, or code can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, libraries, and such, as appropriate. Conversely, the features and functionality of various components can be combined into single components, as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on general or special purpose microprocessors, both, or any other kind of CPU. Generally, a CPU will receive instructions and data from and write to a memory. The essential elements of a computer are a CPU, for performing or executing instructions, and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable storage device, for example, a universal serial bus (USB) flash drive, to name just a few.

Computer-readable media (transitory or non-transitory, as appropriate) suitable for storing computer program instructions and data includes all forms of permanent/non-permanent or volatile/non-volatile memory, media and memory devices, including by way of example semiconductor memory devices, for example, random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices; magnetic devices, for example, tape, cartridges, cassettes, internal/removable disks; magneto-optical disks;

and optical memory devices, for example, digital video disc (DVD), CD-ROM, DVD+/−R, DVD-RAM, DVD-ROM, HD-DVD, and BLURAY, and other optical memory technologies. The memory may store various objects or data, including caches, classes, frameworks, applications, modules, backup data, jobs, web pages, web page templates, data structures, database tables, repositories storing dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, for example, a cathode ray tube (CRT), liquid crystal display (LCD), light-emitting diode (LED), or plasma monitor, for displaying information to the user and a keyboard and a pointing device, for example, a mouse, trackball, or trackpad by which the user can provide input to the computer. Input may also be provided to the computer using a touchscreen, such as a tablet computer surface with pressure sensitivity, a multi-touch screen using capacitive or electric sensing, or other type of touchscreen. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons. These and other UI elements may be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a web browser through which a user can interact with some implementations of the subject matter described in this specification, or any combination of one or more such back-end, middleware, or front-end components. The components of the system can be interconnected by any form or medium of wireline or wireless digital data communication (or a combination of data communication), for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n or 802.20 (or a combination of 802.11x and 802.20 or other protocols consistent with this disclosure), all or a portion of the Internet, or any other communication system or systems at one or more locations (or a combination of communication networks). The network may communicate with, for example, Internet Protocol (IP) packets, Frame Relay frames, Asynchronous Transfer Mode (ATM) cells, voice, video, data, or other suitable information (or a combination of communication types) between network addresses.

The computing system can include clients and servers. A client and server are generally remote from each other and typically interact through a communication network. The relationship of client and server arises by virtue of computer programs running on the respective computers and having a client-server relationship to each other.

Cluster file system involved in this invention can be any file system type accessible from multiple servers for read and update. Locking or consistency tracking is not necessary in this invention since the locking of exchange file system can be done at application layer. Furthermore, Unicode data files are different from non-Unicode data files.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain this disclosure. Other changes, substitutions, and alterations are also possible without departing from the spirit and scope of this disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

What is claimed is:

1. A computer-implemented method, comprising:
    determining demulsifier automation parameters for automating demulsifier injection points of a wet crude handling facility, the determining including performing a data convolution and a smoothening of inlet demulsifier automation parameters; and
    performing the demulsifier automation of the wet crude handling facility, including, for each demulsifier:
        identifying a current state of the demulsifier, the identifying based on the demulsifier automation parameters;
        determining demulsifier calculation input parameters, including performing a convolution and a smoothening of the demulsifier calculation input parameters;
        calculating, using the determined demulsifier calculation input parameters, a demulsifier dosage rate;
        applying, to the demulsifier and based on the current state, a state dependent dosage multiplication factor based on the calculated demulsifier dosage rate.

2. The computer-implemented method of claim 1, wherein states of the demulsifier include a normal state, an abnormal state, and a transit state.

3. The computer-implemented method of claim 2, further comprising performing a state transition from the current state to a new state based on the current state and a determination that a boundary condition has been breached or, when the current state is the transit state, has become normalized.

4. The computer-implemented method of claim 3, wherein state transitions are state-dependent and include:
    a state transition from the normal state to the abnormal state when the boundary condition is breached;
    a state transition from the transit state to the abnormal state when the boundary condition is breached;
    a state transition from the abnormal state to the transit state when the boundary condition is normalized; and
    a state transition from the transit state to the normal state when the boundary condition and the transit setpoint are normal.

5. The computer-implemented method of claim 4, wherein, when the current state is the abnormal state, transitioning to the normal state cannot occur without first transitioning to the transit state.

6. The computer-implemented method of claim 1, wherein the input parameters include a crude temperature and a gas-oil separator plant (GOSP) total liquid flowrate.

7. The computer-implemented method of claim 6, wherein the GOSP total liquid flowrate is a sum of a net crude export rate and a net water injection rate.

8. The computer-implemented method of claim 3, wherein the boundary conditions include threshold values for a temperature, a dehydrator voltage, a desalter voltage, a dehydrator water outlet flow, and a basic sediment and water (BS&W) at a desalter outlet.

* * * * *